United States Patent [19]

Monnier et al.

[11] Patent Number: 5,082,956
[45] Date of Patent: Jan. 21, 1992

[54] ISOMERIZATION OF EPOXYALKENES TO 2,5-DIHYDROFURANS

[75] Inventors: John R. Monnier; Stephen A. Godleski, both of Fairport; Howard M. Low, Rochester; Laughlin G. McCullough, Fairport; Lynda W. McGarry, North Chili, all of N.Y.; Gerald W. Phillips, Longview, Tex.

[73] Assignee: Eastman Kodak COmpany, Rochester, N.Y.

[21] Appl. No.: 627,668

[22] Filed: Dec. 14, 1990

Related U.S. Application Data

[63] Continuation-in-part of Ser. No. 490,208, Mar. 8, 1990, abandoned.

[51] Int. Cl.$^5$ ............................................. C07D 307/28
[52] U.S. Cl. .................................... 549/507; 549/355
[58] Field of Search ............................... 549/507, 355

[56] References Cited

U.S. PATENT DOCUMENTS 3,932,468 1/1976 Kurkov ................................. 549/507
3,996,248 12/1976 Wall et al. ........................... 549/507

OTHER PUBLICATIONS

Crawford et al., Can. J. Chem., 54, 3364–3376 (1976).
Grant and Hackh's Chem. Dictionary, 5th Ed., McGraw-Hill, pp. 175 and 255 (1987).

Primary Examiner—Bernard Dentz
Attorney, Agent, or Firm—J. Frederick Thomsen; William P. Heath, Jr.

[57] ABSTRACT

Disclosed are processes for the isomerization of epoxyalkenes to dihydrofurans by contacting an epoxyalkene with a catalyst comprising a quaternary organic onium iodide compounds, optionally deposited on a non-acidic support and/or in combination with a Lewis acid co-catalyst. The catalyst may comprise a supported catalyst, an unsupported catalyst or a solution of the catalytically-active components in an inert, organic solvent.

33 Claims, No Drawings

ISOMERIZATION OF EPOXYALKENES TO 2,5-DIHYDROFURANS

This application is a continuation-in-part of application Ser. No. 07/490,208 filed Mar. 8, 1990, now abandoned.

This invention pertains to isomerization processes and, more particularly, to processes whereby γ,δ-epoxyalkenes and γ,δ-epoxycycloalkenes are isomerized to obtain the corresponding 2,5-dihydrofuran compounds. This invention also pertains to novel catalyst systems useful in the described isomerization processes and to methods for the preparation of supported catalyst systems.

Dihydrofurans are reactive heterocyclic species which are useful in a variety of applications, e.g., as intermediates in the production of useful polymers and chemicals. However, the use of dihydrofurans for such purposes has heretofore been restricted due to the non-availability of cost-effective preparative procedures therefor.

In addition, dihydrofurans are readily reduced to produce the corresponding tetrahydrofuran species, which are also useful in a variety of applications, e.g., as polar aprotic reaction solvents, co-solvents, reactive intermediates in the production of useful polymers, copolymers, and the like.

U.S. Pat. Nos. 3,932,468 and 3,996,248 disclose the production of 2,5-dihydrofurans by the rearrangement of substituted or unsubstituted epoxyalkenes with a homogeneous catalyst system comprising hydrogen iodide or hydrogen bromide and a transition metal Lewis acid in an organic solvent. This process suffers from a number of disadvantages including the use of corrosive hydrogen halides, the need for expensive, high-boiling tertiary amide solvents, e.g., N-methyl-2-pyrrolidinone, to dissolve the transition metal Lewis acid. We have found that the process of U.S. Pat. Nos. 3,932,468 and 3,996,248 also results in the unwanted production of up to 15% α,β-unsaturated aldehydes or ketones.

The thermal (i.e., non-catalytic) rearrangement of 3,4-epoxy-1-butene has been studied and shown by Crawford et al in the Canadian Journal of Chemistry, Vol. 54, pages 3364–3376 (1976) to produce a variety of products, including 2,3-dihydrofuran, cis and trans 2-butenal and 3-butenal.

Other reactions of epoxides have been reported. See, for example, U.S. Pat. No. 4,600,800, where epoxides are converted to allylic alcohols by contacting an epoxide in the liquid phase with solid alumina catalysts.

Another example of the rearrangement of epoxides is described in the Journal of Organometallic Chemistry, Vol. 359, pages 255–266 (1989), wherein Sato et al report the formation of α,β-unsaturated aldehydes and ketones by the rhodium (I) catalyzed isomerization of 1,3-diene monoepoxides.

U.S Pat. No. 4,897,498 describes an efficient process for the preparation of γ,δ-epoxyalkenes by the selective monoepoxidation of dienes. Thus, a process is needed for the conversion of such epoxyalkenes to dihydrofurans in satisfactory selectivity and/or yields wherein the product may be readily recovered from the catalyst and the catalyst reused and used in continuous operation.

In accordance with the present invention, we have discovered a catalytic process for the isomerization of γ,δ-epoxyalkenes to produce dihydrofurans. The process provides high levels of epoxyalkene conversion with high selectivity to the desired dihydrofuran product. Long catalyst lifetimes are realized and the product may be recovered by relatively simple means since the catalyst and reaction mixture are readily separated by such simple techniques as distillation, decantation, filtration, gas stripping methods, gas/liquid flow separation, and the like.

Our invention also provides novel catalyst systems, both supported and unsupported, which are useful, for example, to promote the isomerization of epoxyalkenes to dihydrofurans. Processes for preparing the supported catalyst systems are also provided herein.

In accordance with the present invention, there is provided a process for the isomerization of γ,δ-epoxyalkenes to the corresponding 2,5-dihydrofuran compounds, which process comprises contacting a γ,δ-epoxyalkene or γ,δ-epoxycycloalkene with a catalytic amount of a quaternary organic onium iodide, e.g., a compound consisting of an ammonium, phosphonium or arsonium cation and an iodide anion, under isomerization conditions of temperature and pressure.

The γ,δ-epoxyalkene and γ,δ-epoxycycloalkene reactants may contain from 4 to about 20 carbon atoms, preferably from 4 to about 8 carbon atoms. Examples of the epoxyalkene and epoxycycloalkene reactants include compounds having the structural formula:

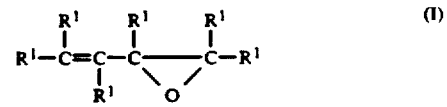

wherein each $R^1$ is independently selected from hydrogen, alkyl of up to about 8 carbon atoms, a carbocyclic or heterocyclic aryl group of about 5 to 10 carbon atoms or halogen or any two $R^1$ substituents collectively may represent an alkylene group forming a ring, e.g., alkylene containing in the main chain up to about 8 carbon atoms. The preferred epoxyalkene reactants comprise compounds of formula (I) wherein only two of the $R^1$ substituents individually may represent lower alkyl, e.g., alkyl of up to about 8 carbon atoms, or collectively represent straight or branched chain alkylene of up to about 8 carbon atoms. Exemplary compounds contemplated for use in the practice of the present invention include 3,4-epoxy-3-methyl-1-butene, 2,3-dimethyl-3,4-epoxy-1-butene, 3,4-epoxycyclooctene, 3,4-epoxy-1-butene, 2,5-dimethyl-2,4-hexadiene monoepoxide, and the like. The epoxyalkene reactant of primary interest is 3,4-epoxy-1-butene.

The 2,5-dihydrofuran compounds obtained in accordance with our novel process have the structural formula:

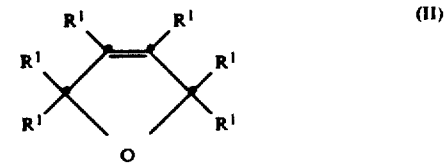

wherein the $R^1$ substituents are defined above. Of the compounds which may be obtained in accordance with our invention, the most important is 2,5-dihydrofuran.

The quaternary onium iodide compounds which may be used as the catalyst in our novel process are known compounds and/or may be prepared according to published procedures. See, for example, U.S. Pat. No. 3,992,432 and the references cited therein. Exemplary quaternary organic onium iodide compounds include mono-, di-, tri-, or tetra-substituted quaternary onium iodides, wherein said substituents are selected from hydrogen, alkyl or substituted alkyl groups, cycloalkyl or substituted cycloalkyl groups, carbocyclic aryl or substituted carbocyclic aryl groups, heteroaryl or substituted heteroaryl groups, ferrocenyl, wherein each of said substituents may be bonded to one another to form a cyclic, heterocyclic, polycyclic or poly-heterocyclic structure. When used on a support or as a melt, the onium compounds normally contain at least 6 carbon atoms, preferably at least 12 carbon atoms, and have melting points not greater than about 225° C., preferably not greater than about 200° C.

Examples of the onium iodide catalysts are compounds conforming to the formulas

(III)

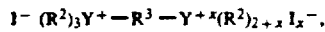
(IV)

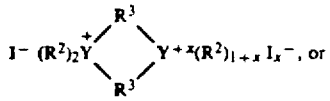
(V)

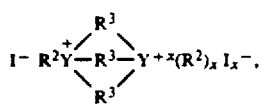
(VI)

wherein
- each $R^2$ independently is selected from hydrogen, alkyl or substituted alkyl moieties having up to about 20 carbon atoms, cycloalkyl or substituted cycloalkyl having about 5 to 20 carbon atoms, or aryl or substituted aryl having about 6 to 20 carbon atoms; or when Y is P, each $R^2$ also may be selected from alkoxy of up to about 20 carbon atoms, cycloalkoxy of about 5 to 20 carbon atoms, aryloxy of 6 to 10 carbon atoms or halogen;
- two or three $R^2$ substituents collectively may represent joined hydrocarbylene groups, e.g. alkylene having 4 to 6 main chain carbon atoms or unsaturated groups such as —CH=CHCH=CHCH= and lower alkyl substituted alkylene and unsaturated groups, which form a mono- or poly-cyclic ring with the Y atom to which they are bonded;
- each $R^3$ is independently selected from hydrocarbylene moieties or substituted hydrocarbylene moieties;
- x is 0 or 1, and
- Y is N, P or As; provided that the quaternary onium iodide compound contains at least 6 carbon atoms. The substituted groups and moieties referred to above bear one or more substituents such as groups having the formulas

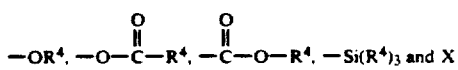

wherein each $R^4$ is independently selected from hydrogen or alkyl of up to about 20 carbon atoms and X is halogen. As used herein, the terms "hydrocarbylene moieties" refers to alkylene moieties having up to about 6 carbon atoms, arylene or polyarylene moieties having 6 to 20 carbon atoms.

The preferred onium iodide catalysts are the quaternary ammonium and quaternary phosphonium iodide compounds. Exemplary ammonium compounds include tetrapentylammonium iodide, tetrahexylammonium iodide, tetraoctylammonium iodide, tetradecylammonium iodide, tetradodecylammonium iodide, tetrapropylammonium iodide, tetrabutylammonium iodide, monooctylammonium iodide, dioctylammonium iodide, trioctylammonium iodide, N-octylquinuclidinium iodide, N,N'-dimethyl-N,N'-dihexadecylpiperazinium diiodide, dimethylhexadecyl-[3-pyrrolidinylpropyl]ammonium iodide, N,N,N,N',N',N'-hexa(dodecyl)octane-1,8-diammonium diiodide, N,N,N,N',N',N'-hexa(dodecyl)butane-1,4-diammonium diiodide, N-octylpyridinium iodide, and the like.

Exemplary phosphonium compounds include tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)phosphonium iodide, tetrakis(2-methylpropyl)phosphonium iodide, tris(2-methylpropyl)(butyl)phosphonium iodide, triphenyl(3,3-dimethylbutyl)phosphonium iodide, triphenyl(3-methylbutyl)phosphonium iodide, tris(2-methylbutyl)(3-methylbutyl)phosphonium iodide, triphenyl[2-trimethylsilylethyl]phosphonium iodide, tris(p-chlorophenyl)(dodecyl)phosphonium iodide, hexyltris(2,4,6-trimethylphenyl)phosphonium iodide, tetradecyltris(2,4,6-trimethylphenyl)phosphonium iodide, dodecyltris(2,4,6-trimethylphenyl)phosphonium iodide, and the like.

Tetra-substituted ammonium and phosphonium iodide compounds containing a total of about 16 to 60 carbon atoms are especially preferred. Such compounds have the formulas

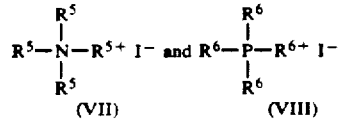
(VII)     (VIII)

wherein
- each $R^5$ substituent independently is selected from alkyl of up to about 20 carbon atoms and each $R^6$ substituent is independently selected from $R^5$, benzyl, phenyl or phenyl substituted with up to 3 substituents selected from lower alkyl (alkyl of up to about 4 carbon atoms) lower alkoxy or halogen; or
- two $R^5$ substituents collectively may represent alkylene of 4 to 6 carbon atoms including alkylene of 4 to 6 carbon atoms substituted with lower alkyl; provided, as specified above, that the quaternary iodide compounds contain about 16 to 60 carbon atoms.

Another group of preferred ammonium iodide compounds are comprised of N-alkyl-azabicycloalkane and N-alkyl- and N,N'-dialkyl-diazabicycloalkane iodide compounds containing 6 to about 12 ring carbon atoms, e.g., bicyclic compounds having the general formula

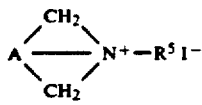

(IX)

wherein $R^5$ is defined above and A is the residue of an azabicycloalkane or diazabicycloalkane having 6 to 12 ring carbon atoms (including the 2 carbon atoms in the above general formula), e.g., azabicyclooctane, azabicyclononane, diazabicyclooctane and the like.

The onium iodide compounds described hereinabove may be employed in combination with a Lewis acid to catalyze the isomerization process of our invention. Examples of such optional Lewis acid co-catalysts include the alkali metal halides, zinc halides, magnesium halides, tin (II) halides, tin (IV) halides, titanium (IV) halides, titanium (IV) tetra-lower-alkoxides, zirconium (IV) halides, manganese (II) halides, iron (III) halides, or iron (III) acetylacetonate. Preferably, the Lewis acid co-catalyst is an alkali metal iodide, zinc iodide, zinc chloride, magnesium iodide, tin (II) iodide, tin (IV) iodide, titanium (IV) iodide, titanium (IV) tetramethoxide, titanium (IV) tetraethoxide, titanium (IV) tetraisopropoxide, zirconium (IV) iodide, manganese (II) iodide, manganese (II) chloride, iron (III) iodide, iron (III) acetylacetonate or a combination thereof. The Lewis acid co-catalysts which are particularly preferred are polarizable iodides, such as, for example, titanium (IV) iodide, zirconium (IV) iodide, and, especially, zinc iodide and tin (II) iodide.

The Lewis acid co-catalyst alternatively may be selected from organotin (IV) and organoantimony (V) compounds such as hydrocarbyltin trihalides, dihydrocarbyltin dihalides, trihydrocarbyltin halides, tetrahydrocarbyltin compounds and tetrahydrocarbylantimony halides. Examples of such organometallic compounds include compounds having the formula

wherein
each $R^7$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms;
Hal is a halogen atom such as bromo or, preferably, iodo; and
n is 1, 2, 3 or 4.

Examples of organometallic compounds include dibutyltin diiodide, tributyltin iodide, trioctyltin iodide, triphenyltin iodide, tributyltin bromide, trimethyltin iodide, butyltin triiodide, tetrabutyltin, tetraoctyltin, triphenyltin iodide, tribenzyltin iodide, dimethyltin diiodide, diphenyltin diiodide, triphenyltin bromide and tetraphenylantimony iodide.

The preferred organometallic compounds comprise tin (IV) iodides having the above general formula and a total carbon content of about 3 to 24 carbon atoms wherein
each $R^7$ substituent independently is selected from alkyl of up to about 12 carbon atoms, benzyl, phenyl or phenyl substituted with up to 3 substituents selected from lower alkyl, lower alkoxy or halogen;
Hal is iodo; and
n is 2 or 3.

The quaternary organic onium iodide catalyst, or the quaternary organic onium iodide-Lewis acid catalyst system, may be employed in the process provided by this invention in either a supported or unsupported form. The supported catalysts of this invention comprise an essentially non-acidic catalyst support material having one or more quaternary organic onium iodide compounds distributed on the surface thereof as a substantially continuous and uniform film and, optionally, one or more of the Lewis acids described above, e.g., an alkali metal halide, zinc halide, magnesium halide, tin (II) halide, tin (IV) halide, titanium (IV) halide, titanium (IV) lower alkyl alkoxide, organotitanium (IV) halide, zirconium (IV) halide, manganese (II) halide, iron (III) halide, iron (III) acetylacetonate or one of the organotin compounds or organoantimony halides described hereinabove.

The essentially non-acidic support may be in the form of a powder or shaped material having sufficient structural integrity to allow passage of gaseous reactant through a packed or fluidized bed of the supported catalyst under reaction conditions. Preferred support materials employed in the practice of the present invention are materials having a particle size in the range of about 20 up to 200 microns and having a crush strength of at least about two pounds. Support materials having crush strengths of at least ten pounds are especially preferred.

A variety of shapes are suitable for use as the support material employed in the practice of the present invention. For example, pellets, spheres, rings, saddles, extruded cylinders, and the like can be employed, so long as such materials have dimensions and packing characteristics so as to allow for the ready passage of gaseous reactant and product through a packed or fluidized bed of the catalyst under reaction conditions.

Examples of the materials which may be employed as the support include zinc oxide, zinc carbonate, magnesium oxide, silica, alumina, titanium oxide, lanthanum oxide, boron nitride, boron carbide, silicon nitride, silicon carbide, tin oxide, calcium oxide, barium oxide, strontium oxide, zirconium oxide, carbon, boron phosphate, or zirconium phosphate, as well as mixtures of any two or more thereof. The preferred support materials contemplated for use in the practice of the present invention include zinc oxide, zinc carbonate, magnesium oxide, silica, alumina, titanium oxide, boron nitride, silicon nitride, silicon carbide, calcium oxide, barium oxide and carbon as well as mixtures of any two or more thereof. Silica, alumina, titanium oxide and zinc oxide are particularly preferred support materials.

The amount of the quaternary organic onium iodide component of the novel catalyst compositions of this invention can vary substantially depending, for example, on the particular support material and the form, e.g., surface area, thereof, the mode in which the isomerization process is operated, the particular quaternary onium iodide present, the presence or absence of a Lewis acid co-catalyst, etc. The amount of the onium iodide, calculated as weight iodide, typically will be in the range of about 0.1 to 30 weight percent based on the total weight of the catalyst. Preferred loading levels fall in the range of about 0.5 up to 20 weight percent (same basis).

When present, the quantity of Lewis acid component of the catalyst compositions generally is in the range of about 0.01 to 30 weight percent, based on the total weight of the catalyst. The preferred quantity of the inorganic Lewis acid co-catalysts, e.g., titanium (IV) iodide, zirconium (IV) iodide, zinc iodide and tin (II) iodide, is in the range of about 0.02 up to 5.0 weight percent based on the total weight of the catalyst.

Another embodiment of the catalyst compositions provided by our invention comprise a support material having deposited thereon (i) about 0.1 to 30 weight percent of an organic onium iodide and (ii) about 0.01 to 30 weight percent of an organotin (IV) compound or organoantimony (V) halide, based on the total weight of the catalyst composition. These catalyst compositions preferably comprise:

(i) about 0.5 to 20 weight percent of a tetra-substituted ammonium and/or phosphonium iodide compound of formula (VII) and/or (VIII); and (ii) about 0.02 to 20 weight percent of an organotin iodide containing a total of about 3 to 24 carbon atoms and having the formula

wherein each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3; on (iii) a support material selected from silica, alumina, zinc oxide, titanium oxide, boron nitride and silicon carbide.

The supported catalysts described herein may be prepared by a variety of procedures as will be readily apparent to those skilled in the art. For example, the supported catalysts may be prepared by the steps comprising:

(a) impregnating a suitable support with a solution of one or more quaternary organic onium iodide compound and, optionally, one or more Lewis acids, and thereafter (b) removing the solvent from the impregnated support.

Solvents contemplated for use in the impregnation step include polar solvents capable of substantially dissolving the quaternary organic onium iodide and the optionally employed Lewis acid. Such solvents include water, lower alcohols such as methanol, ethanol, isopropyl alcohol, and the like. Preferred solvents are those which can be easily removed by standard evaporative techniques once the desired impregnation has been carried out.

The volume of solvent required is 0.5 to 20.0 ml of solvent (plus quaternary organic onium iodide and, optional Lewis acid) per gram of support, the minimum volume of solvent being defined as that volume required to cover the catalyst support. The support and impregnation solution are agitated (typically by rotary tumbling) for 0.2 to 2.0 hrs at slightly elevated temperatures, e.g., 20° to 60° C., to maximize interaction of support and catalytic components. The solvent is preferentially removed by rotary evaporation at reduced pressure at temperatures ranging from 40° to 100° C., or alternatively by drying in a heated forced air oven, or further alternatively by spray-drying the catalyst solution on the support. After drying, the catalyst is ready to be loaded into a reactor.

Prior to contacting the catalyst with an epoxyalkene under isomerization conditions, the catalyst optionally may be subjected to pre-treatment conditions of time and temperature sufficient to activate said catalyst relative to non-pretreated catalyst. Typical pre-treatment conditions of time and temperature comprise a temperature at least as high as the melting point of said quaternary organic onium iodide, but no greater than 225° C., for a time in the range of about 0.1 up to 10 hours.

The conditions of temperature and pressure and the space velocity employed in our novel isomerization process can vary considerably depending on various factors such as the activity of the catalyst used, the degree of conversion and/or selectivity desired, the gas hour space velocity employed, the mode of operation and the like. For example, the process may be carried out at a temperature in the range of about 60° to 225° C. although temperatures of about 100° to 200° C. are more typical. The total reaction pressure may be in the range of about 1.02 to 70 bar (absolute) with the preferred range being about 1.1 to 20 bar total pressure.

The gas hourly space velocity may be varied substantially, e.g., from about 1 to about 10,000, although our process normally is performed using gas hourly space velocities in the range of about 10 up to 5,000 $(hr^{-1})$. The epoxyalkene reactant may constitute up to 100% of the feed composition or may be fed along with an inert diluent wherein volume ratio of the epoxyalkene:inert diluent can vary over a wide range of values, typically within 1:100 to 4:1. Exemplary inert gas diluents include helium, argon, nitrogen, carbon dioxide, or hydrocarbons which are gaseous under reaction conditions. Preferably, the epoxyalkene concentration is in the range of about 5 up to 80 volume percent of the feed composition.

The isomerization process may be carried out using the catalysts described herein either in a supported or unsupported form. Thus, the supported catalysts may be utilized in fixed or fluidized beds using reactor configurations well-known to those skilled in the art.

When the catalyst is unsupported, it can be used at temperatures either below, at or above the melting point of the quaternary organic onium iodide salt. When the catalyst is at or above its melting point and exists as a substantially liquid phase, it is necessary to maintain the catalyst in a reactor volume such that the passage of the gaseous feed and product molecules is not restricted, yet contains the catalyst in the reactor volume. An up-flow reactor is suitable for this purpose since the gaseous feed maintains the catalyst in the appropriate position in the reactor, yet permits the passage of unreacted feed and reaction products through the liquid, or substantially liquid, phase catalyst and into the downstream refining/recycle apparatus. In an especially preferred mode of operation, the catalyst is in a vessel with a closed bottom and the feed is added through a gas dispersion apparatus below the level of the catalyst. The unreacted feed and reaction products can exit from the top of the reactor.

The unsupported catalyst system preferably is used in our process as a melt of an intimate mixture of one or more of the quaternary onium iodide compounds and, optionally, one or more of the Lewis acid co-catalysts described hereinabove. The onium iodide:co-catalyst weight ratio of the unsupported catalyst system can vary substantially, e.g. from 500:1 to 1:100, depending on the particular co-catalyst selected. The preferred onium iodide:co-catalyst weight ratios depend on whether the co-catalyst is (1) an organotin (IV) compound or an organoantimony (V) halide or (2) one of the other Lewis acids described herein above. Thus, for the unsupported catalyst systems containing an inorganic Lewis acid, such as titanium (IV) iodide, zirconium (IV) iodide, zinc iodide and tin (II) iodide, the preferred onium iodide:co-catalyst weight ratio is about 200:1 to 5:1 and for the organotin (IV) compounds and organoantimony (V) halides the preferred onium iodide:co-catalyst weight ratio is about 1:100 to 50:1. Particularly preferred unsupported catalyst systems comprise a mixture of one or more of the tetra-substituted ammonium or phosphonium iodide compounds described hereinabove and tin (II) iodide, zinc iodide or an organotin iodide.

The unsupported quaternary organic onium iodide and/or Lewis acid catalyst may be used with an inert organic solvent if desired to alter the reaction conditions and/or reactor configuration. The optional, inert organic solvent may be used, for example, to change the concentration of the quaternary organic onium iodide and/or the Lewis acid or to assist in heat and/or mass transfer characteristics of the catalytic process.

Thus, another embodiment of our invention comprises the isomerization of an epoxyalkene to the corresponding 2,5-dihydrofuran in the presence of a homogeneous catalyst solution. This embodiment may be carried out in the presence of one or more of the above-described organometallic compounds although reaction rates are relatively slow if an organic onium iodide is not included. Accordingly, the homogeneous catalyst solution preferably comprises a catalytic amount of (i) one or more of the above-described organometallic compounds and (ii) one or more of the above-described organic onium iodides in (iii) an inert organic solvent, i.e., a solvent which does not react with the γ,δ-epoxyalkene or γ,δ-epoxycycloalkene reactants or the 2,5-dihydrofuran products. Examples of the solvents which may be used include aliphatic and aromatic hydrocarbons such as heptane, toluene, specific or mixed xylenes, pseudocumene, and mesitylene; halogenated hydrocarbons such as chlorobenzene, 1,2-dichlorobenzene, and 1,1,2,2-tetrachloroethane; ketones such as cyclohexanone, 5-methyl-2-hexanone, and 2-heptanone; ethers such as 2,5-dihydrofuran, tetrahydrofuran, and bis(2-methoxyethyl)ether; esters such as isobutyl acetate; and tertiary amides such as N-methyl-2-pyrrolidinone, N-cyclohexyl-2-pyrrolidinone, N-ethyl-2-pyrrolidinone, and N,N-dimethylacetamide. Normally, for ease of separation, the solvent or mixture of solvents employed have boiling points at least 20° C. above the boiling point of the 2,5-dihydrofuran product and the unsaturated aldehyde or ketone by-products.

The concentrations of the organometallic compound and the optional onium iodide in the inert, organic solvent can be varied substantially depending, for example, on the particular catalytically-effective components present, the design of the reactor system, etc. Typically, the concentration of the organometallic compound will be about 1 to 50 weight percent and the concentration of the onium iodide compound, when present, will be about 1 to 70 weight percent, both concentrations being based on the total weight of the catalyst solution. Normally, the mole ratio of onium iodide to organometallic compound is at least 1:1.

The preferred catalyst solutions comprise (i) about 1 to 25 weight percent of an organotin iodide containing about a total of about 3 to 24 carbon atoms and having the formula

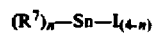

wherein
each $R^7$ substituent independently is selected from alkyl of up to about 8 carbon atoms, benzyl, phenyl or phenyl substituted with up to 3 substituents selected from lower alkyl, lower alkoxy or halogen; and
n is 1, 2, 3 or 4; and
(ii) about 1 to 25 weight percent of a tetrasubstituted ammonium or phosphonium iodide of formula (VII) and/or (VIII); and
(iii) an inert organic solvent selected from hydrocarbons and chlorinated hydrocarbons having up to about 10 carbon atoms.

Toluene, mixed or specific xylene isomers, chlorobenzene, mixed or specific dichlorobenzene isomers, pseudocumene, and mesitylene are particularly preferred solvents.

The isomerization process may be carried out in the liquid phase using the catalyst solutions described hereinabove by contacting a γ,δ-epoxyalkene or γ,δ-epoxycycloalkene at a temperature of about 50° to 200° C., preferably about 100° to 150° C., depending on the solvent or mixture of solvents employed. The process may be carried out at atmospheric or super-atmospheric pressures, e.g., up to about 22 bar (absolute).

The process employing the catalyst solution may be carried out in a batch, semi-continuous or continuous mode of operation. For example, batch operation may comprise refluxing a mixture of the γ,δ-epoxyalkene and catalysts, e.g. tributyltin iodide and tetraheptyl ammonium iodide, in a solvent such as p-xylene for a time sufficient to convert essentially all the epoxide to the 2,5-dihydrofuran. The products are then separated by distillation from the mixture. The undistilled catalyst solution may be reused in a subsequent reaction.

The catalyst solution preferably is employed in a continuous mode of operation wherein a γ,δ-epoxyalkene or γ,δ-epoxycycloalkene is added to a recirculated catalyst solution which is then introduced into a continuous reactor. After isomerization, the reaction stream is fed to a distillation system for removal of product or products and recycle of the catalyst solution. Examples of continuous reactor designs in which the process can be performed are continuous stirred tank reactors and plug flow reactors.

Our novel isomerization process and the catalyst systems, compositions and solutions useful in practicing the process are further illustrated by the following examples.

PREPARATION OF CATALYSTS

EXAMPLE 1

Tetrabutylammonium iodide (1.786 g) was dissolved at 25° C. in ethyl alcohol (80 mL) in a 250 mL, round bottom flask. Zinc oxide (5.0 g, ultrapure) powder was added and the mixture was agitated for twenty minutes at 40° C. on a rotary evaporator. The zinc oxide used had a surface area of 3.8 square meters per g (m²/g) and a particle diameter in the range of 75 to 150 microns. The alcohol was then removed on the rotary evaporator at 40° C. under vacuum. The supported catalyst obtained contained 18.2 weight percent tetrabutylammonium iodide.

EXAMPLE 2

Tetradodecylammonium iodide (51.24 g), zinc iodide (1.06 g) and ethyl alcohol (200 mL) were placed in a one-liter, fluted flask and placed on a rotary evaporator and agitated for five minutes in a 60° C. bath. Silica extrusions (400 g, Calsicat $SiO_2$ pellets, 3/16" diameter having a surface area of approximately 0.5 $m^2/g$ and a general composition of 100% $SiO_2$) were then added and agitation continued for twenty minutes in the bath at 60° C. The alcohol was then removed on the rotary evaporator at 60° C. under vacuum. The supported catalyst obtained contained 11 weight percent tetradodecylammonium iodide and 0.23 weight percent zinc iodide.

EXAMPLE 3

Triphenyl(hexyl)phosphonium iodide (0.250 g) and zinc iodide (0.0050 g) were placed in a 50.mL flask and then silica (2.0 g) was added. The silica support material was prepared by grinding the silica extrudate described in Example 2 and classifying the ground material and using the portion which passed a 10 mesh sieve and was retained on a 20 mesh. The flask was placed on a rotary evaporator and agitated for 20 minutes with the flask in the bath at 60° C. Methanol was removed while the flask was in the 60° C. bath using vacuum. The supported catalyst obtained (2.25 g) contained 11 weight percent triphenyl(hexyl)phosphonium iodide and 0.11 weight percent zinc iodide.

The catalyst compositions set forth in the examples of Table I were prepared using the procedures described in the preceding examples. The Weight Percent given in Table 1 refers to the weight percent of the quaternary onium iodide present based on the total weight of the catalyst. The zinc oxide and silica used as the support materials were the same as the support materials described in Examples 1 and 3.

TABLE I

| Example | Quaternary Onium Iodide | Support | Weight Percent |
|---|---|---|---|
| 4 | Tetrapropylammonium iodide | ZnO | 15.8 |
| 5 | Tetrabutylammonium iodide | ZnO | 22 |
| 6 | Tetrapentylammonium iodide | ZnO | 20.4 |
| 7 | Tetrahexylammonium iodide | ZnO | 22.5 |
| 8 | Tetraoctylammonium iodide | ZnO | 26.0 |
| 9 | Tetradecylammonium iodide | ZnO | 18.0 |
| 10 | Tetradodecylammonium iodide | ZnO | 21.0 |
| 11 | Trioctylammonium iodide | ZnO | 21.0 |
| 12 | Dioctylammonium iodide | ZnO | 18.0 |
| 13 | Octylammonium iodide | ZnO | 13.0 |
| 14 | N,N'-Dimethyl-N,N'-hexadecylpiperizinium diiodide | ZnO | 20.0 |
| 15 | N,N-Dimethyl-N-hexadecyl-N-[3-pyrrolidinonopropyl]-ammonium iodide | ZnO | 19.0 |
| 16 | N,N,N,N',N',N'-hexa-(dodecyl)-octane-1,4-diammonium diiodide | ZnO | 30.0 |
| 17 | N,N,N,N',N',N'-hexa-(dodecyl)-butane-1,4-diammonium diiodide | ZnO | 29.0 |
| 18 | N-Octylpyridinium iodide | ZnO | 16.0 |
| 19 | Tetraoctylphosphonium iodide | $SiO_2$ | 11.0 |
| 20 | Tetrabutylphosphonium iodide | $SiO_2$ | 11.0 |
| 21 | Tetradodecylammonium iodide | $SiO_2$ | 11.0 |

The catalysts set forth in Table II were prepared from a quaternary onium iodide compound, a Lewis acid co-catalyst and a support material according to the procedures described in Examples 1-3. The Weight Percent given for each example refers to the weight of the co-catalyst present on the supported catalyst based on the total weight of the catalyst. The materials described in Examples 1 and 3 were used as the catalyst supports. The onium iodide compound and the weight percent thereof present on each catalyst and the support material of each of the Table II examples were:

TABLE II

| Example | Co-catalyst | Weight Percent |
|---|---|---|
| 22 | $ZnI_2$ | 0.22 |
| 23 | $ZnCl_2$ | 0.22 |
| 24 | $SnI_2$ | 0.27 |
| 25 | $SnI_2$ | 0.54 |
| 26 | $SnI_2$ | 1.10 |
| 27 | $MgI_2$ | 0.22 |
| 28 | $MnI_2$ | 0.22 |
| 29 | $ZrI_4$ | 0.27 |
| 30 | $TiI_4$ | 0.22 |
| 31 | Titanium tetraisopropoxide | 0.22 |
| 32 | Iron (III) acetylacetonate | 0.11 |
| 33 | $ZnI_2$ | 1.7 |
| 34 | $SnI_2$ | 2.2 |
| 35 | $SnI_4$ | 1.8 |
| 36 | LiI | 1.5 |
| 37 | $ZnI_2$ | 0.9 |
| 38 | $ZnI_2$ | 3.4 |
| 39 | $ZnI_2$ | 8.5 |
| 40 | $SnI_2$ | 0.27 |
| 41 | $SnI_2$ | 0.54 |
| 42 | $SnI_2$ | 1.1 |
| 43 | $ZnI_2$ | 0.055 |
| 44 | $ZnI_2$ | 0.11 |
| 45 | $ZnI_2$ | 0.15 |
| 46 | $ZnI_2$ | 0.23 |
| 47 | $ZnI_2$ | 0.55 |
| 48 | $SnI_2$ | 0.11 |
| 49 | $ZnI_2$ | 0.11 |
| 50 | $ZnI_2$ | 0.55 |
| 51 | $ZnI_2$ | 2.3 |

Examples 22-32: 11% Tetradodecylammonium iodide on $SiO_2$
Examples 33-42: 26% Tetraoctylammonium iodide on ZnO
Examples 43-48: 11% Tetraoctylphosphonium iodide on $SiO_2$
Examples 49-51: 11% Tetrabutylphosphonium iodide on $SiO_2$ The supported catalysts described in Example 52-57 were prepared by procedures analogous to Example 3 using the silica support material described in Example 3, zinc iodide and the quaternary ammonium iodide compound given in each example. Each catalyst contained 11 weight percent of the quaternary ammounium iodide compound and 0.11 weight percent zinc iodide, based on the total weight of the catalyst.

EXAMPLE 52

N-Hexyl-1,4-diazabicyclo[2.2.2]octane iodide

EXAMPLE 53

N-Tetradecyl-1,4-diazabicyclo[2.2.2]octane iodide

EXAMPLE 54

N-Hexyl-1,4-diazabicyclo[2.2.2]octane iodide hydroiodide

EXAMPLE 55

N-Octylazabicyclo[2.2.2]octane iodide

EXAMPLE 56

N-Methyl-N-dodecylpyrrolidinium iodide

EXAMPLE 57

Tetrakis-(3-methylbutyl)ammonium iodide

The supported catalysts described in Example 58–71 were prepared by procedures analogous to and using the silica support material described in Example 3, zinc iodide and the quaternary phosphonium iodide compound given in each example. Each catalyst contained 11 weight percent of the quaternary phosphonium iodide compound and 0.11 (Examples 58 and 60) or 0.055 (Examples 59 and 61–72) weight percent zinc iodide, based on the total weight of the catalyst.

EXAMPLE 58
Tribenzyl(octyl)phosphonium iodide

EXAMPLE 59
Triphenyl(hexyl)phosphonium iodide

EXAMPLE 60
Tribenzyl(dodecyl)phosphonium iodide

EXAMPLE 61
Triphenyl(octyl)phosphonium iodide

EXAMPLE 62
Triphenyl(decyl)phosphonium iodide

EXAMPLE 63
Triphenyl(dodecyl)phosphonium iodide

EXAMPLE 64
Tris(2-methylpropyl)(butyl)phosphonium iodide

EXAMPLE 65
Tris(2-methylpropyl)(3-methylbutyl)phosphonium iodide

EXAMPLE 66
Tris(3-chlorophenyl)(dodecyl)phosphonium iodide

EXAMPLE 67
Triphenyl(3-methylbutyl)phosphonium iodide

EXAMPLE 68
Triphenyl(trimethylsilylmethyl)phosphonium iodide

EXAMPLE 69
Tris(2,4,6-trimethylphenyl)(hexyl)phosphonium iodide

EXAMPLE 70
Tris(2,4,6-trimethylphenyl)(dodecyl)phosphonium iodide

EXAMPLE 71
Tris(2,4,6-trimethylphenyl)(tetradecyl)phosphonium iodide

EXAMPLE 72
Tetrakis(2-methylpropyl)phosphonium iodide

EXAMPLE 73
Silica support material described in Example 3 was contacted with tetraoctylphosphonium iodide, tetradodecylammonium iodide and zinc iodide to obtain a supported catalyst bearing 5.5 weight percent tetraoctylphosphonium iodide, 5.5 weight percent tetradodecylammonium iodide and 0.22 weight percent zinc iodide.

Examples 74–83 describe supported catalysts prepared from a quaternary ammonium compound and a variety of support materials. The percent given in each of the examples refers to the weight percent of the quaternary ammonium compound specified on the support based on the total weight of the catalyst. The catalysts of Examples 78–83 also contained 0.23 weight percent zinc iodide.

EXAMPLE 74
26% Tetraoctylammonium iodide on silicon nitride powder having a surface area of 11.9 $m^2/g$ and a mean particle size of 60 microns.

EXAMPLE 75
26% Tetraoctylammonium iodide on boron nitride powder having a surface area of 2.9 $m^2/g$, a bulk density of 2.1 $g/cm^3$ and a particle diameter in the range of 50–100 microns.

EXAMPLE 76
22% Tetrabutylammonium iodide on zinc carbonate powder having a particle diameter in the range of 75–150 microns.

EXAMPLE 77
22% Tetrabutylammonium iodide on magnesium oxide powder having a surface area of 1.0 $m^2/g$ and a particle diameter in the range of 75–150 microns.

EXAMPLE 78
11% Tetradodecylammonium iodide on alumina (Calsicat SE) spheres: ⅛" diameter spheres with a surface area of 10 $m^2/g$, a total pore volume =0.44 cc (Hg)/g, packing density of 0.81 $g/cm^3$, crush strength =18 lbs, and a general composition by weight percent of: $Al_2O_3$=99.7, $SiO_2$=0.1, $Na_2O$=0.1 and $Fe_2O_3$=0.08.

EXAMPLE 79
11% Tetradodecylammonium iodide on alumina (Norton 5552) rings ¼" rings having a surface area of 0.43 $m^2/g$, a total pore volume of 0.37 cc (Hg)/gm, a median pore diameter of 7µ, a packing density of 0.80 $g/cm^3$, and a chemical composition by weight percent of: $Al_2O_3$=93.1, $SiO_2$=5.6, $Fe_2O_3$=0.3, $TiO_2$=0.1, CaO=0.1, MgO=0.3, $Na_2O$=0.1, $K_2O$=0.1.

EXAMPLE 80
11% Tetradodecylammonium iodide on alumina (Norton 08228) pellets: 3/16" diameter pellets with a surface area of 0.25 $m^2/g$, a total pore volume of 0.23 cc (Hg)/gm, a median pore diameter of 19µ, a packing density of 0.90 $g/cm^3$, and a chemical composition by weight percent of: $Al_2O_3$=84.7, $SiO_2$=13.4, $Fe_2O_3$=0.21, $TiO_2$=0.47, CaO=0.21, MgO=0.12, $Na_2O$=0.15, $K_2O$=0.26.

EXAMPLE 81
11% Tetradodecylammonium iodide on zinc oxide (Calsicat ZnO) extrudate: ⅛" diameter extrudate with a surface area of 3.0 $m^2/g$, a packing density of 1.5 $g/cm^3$, a crush strength of 11 pounds, and a nominal chemical composition of 100% ZnO.

EXAMPLE 82
18% Tetradecylammonium iodide on alumina (Norton 82326) spheres: 3/16" diameter spheres having a surface area of 0.39 m$^2$/g, a total pore volume of 0.36 cc(Hg)/g, a median pore diameter of 5.4 microns, a packing density of 0.94 g/cm$^3$, and a chemical composition by weight percent of: Al$_2$O$_3$=93.1, SiO$_2$=5.6, Fe$_2$O$_3$=0.3, MgO=0.3, TiO$_2$=0.1 and Na$_2$O=0.1.

EXAMPLE 83

18% Tetradecylammonium iodide on titanium dioxide (Degussa) extrudate: 1/16" diameter extrudate having a surface area of 50 m$^2$/g and a chemical composition by weight percent of: TiO$_2$=99.5, Al$_2$O$_3$=0.3, and SiO$_2$=0.2.

The following examples illustrate the preparation of the catalyst compositions comprising an organic onium iodide and an organotin halide on a catalyst support material.

EXAMPLE 84

Triphenyl(hexyl)phosphonium iodide (0.75 g) and triphenyltin iodide (0.0151 g) were placed in a 50 mL flask and dissolved in 30 mL of anhydrous methanol at 30° C. To this solution was added 6.0 g of silica support. The silica support material was prepared by grinding silica pellets 0.1875 inch in diameter and classifying the ground material and using the portion which passed a 10 mesh sieve and was retained on a 20 mesh. The flask was placed on a rotary evaporator and agitated for 20 minutes with the flask in the bath at 50° C. Methanol was removed while the flask was in the 60° C. bath using vacuum. The supported catalyst obtained (6.75 g) contained 11 weight percent triphenyl(hexyl)phosphonium iodide and 0.22 weight percent triphenyltin iodide.

EXAMPLE 85

A supported catalyst consisting of 11 weight percent tetradodecylammonium iodide and 0.22 weight percent tributyltin iodide on silica was prepared according to the general procedure described in Example 84.

EXAMPLE 86

A supported catalyst consisting of 11 weight percent tetradodecylammonium iodide and 1.1 weight percent triphenyltin iodide on silica was prepared according to the general procedure described in Example 84.

ISOMERIZATION OF EPOXYBUTENES

The supported catalysts described hereinabove were used to isomerize 3,4-epoxy-1-butene under steady state conditions in a 1 atmosphere, single-pass flow reactor system. The reactor tube was constructed of Pyrex glass and the catalyst charge (between 0.1 and 20.0 g) was held in place by means of a Pyrex glass frit. The geometries of the reactor and catalyst particles as well as bed depth were chosen to maintain and measure the true kinetic and catalytic aspects of the reaction. Gas hourly space velocities (GHSV, mL gas fed per hour per mL catalyst) for all experiments fell within the range of about 30 up to 3000. A chromel/alumel thermocouple sheathed in stainless steel was embedded within the catalyst bed to measure the true reaction temperature.

The 3,4-epoxy-1-butene reactant was added by flowing helium through a liquid-vapor saturator containing the liquid reactant. The reactant was maintained at constant temperature by coupling the saturator to a refrigerated constant temperature circulator bath which was capable of maintaining the temperature of the liquid-vapor saturator at ±1° C. accuracy from −10° C. to +120° C. The helium flow used to sweep the 3,4-epoxy-1-butene vapor from the saturator to the reactor inlet was maintained using a mass flow controller over the range 2-100 mL (standard temperature and pressure) per minute. The feed compositions fed to the reactor consisted of from 0.01 to 0.33 bar 3,4-epoxy-1-butene pressure (absolute) with the balance He to give a total pressure of approximately 1 to 1.5 bar at GHSV ranging from 30 to 3000. Reaction product analyses (as well as feed composition analyses) were made using an in-line gas sampling loop connected directly to the inlet of a Varian 3760 gas chromatograph. The reaction products were analyzed using a packed Chromosorb 101 column (8 feet by 2 mm interior diameter Pyrex glass capillary column) connected to a flame ionization detector.

Further, by means of a switching valve, it was possible to divert the feed stream through the in-line sample loop prior to passage over the catalyst. In this way, quantitative analysis of the feed stream and comparison to the corresponding data from the reactor effluent were possible, thereby providing very accurate measurements of both conversion levels and product selectivities. Output from the flame ionization (FI) detector was integrated using a computing integrator which was programmed to give both absolute quantities and rates of formation. All reactor exit lines were heated and maintained at 125°-140° C. to prevent product condensation.

The GC analysis was performed using the following temperature programming schedule: an initial temperature of 100° C. was held for 2 minutes, followed by a temperature program rate of +10° C. per minute up to a final temperature of 200° C. which was held for 7 minutes. The helium GC carrier rate was 20 mL per minute.

The catalyst and conditions employed and the results obtained in each of the isomerization experiments are set forth in Tables III and IV wherein Temp is the temperature in ° C. at which the reaction occurred, Press is the 3,4-epoxy-1-butene partial pressure in bars absolute of the gas fed, GHSV is defined above, Conv is the mole percent of moles 3,4-epoxy-1-butene converted to other compounds per moles of 3,4-epoxy-1-butene fed and Select is the mole percent of 3,4-epoxy-1-butene converted to 2,5-dihydrofuran based on the moles of 3,4-epoxy-1-butene converted.

EXAMPLE 87-114

These examples demonstrate the use of supported catalysts bearing only a quaternary onium iodide as the catalytic component. In Examples 87-96 and Examples 99-101 the catalysts were subjected to a pretreatment at elevated temperatures in an inert atmosphere for 30-60 minutes prior to starting the reactant feed. The pretreatments were performed at 140° C. except in Examples 87 and 88 wherein temperatures of 160° C. and 150° C., respectively, were used.

TABLE III

| Example | Catalyst of Example | Temp | Press | GHSV | Conv | Select |
|---|---|---|---|---|---|---|
| 87 | 4 | 130 | 0.03 | 240 | 6 | 21 |
| 88 | 1 | 140 | 0.03 | 240 | 48 | 68 |
| 89 | 5 | 140 | 0.03 | 240 | 49 | 68 |
| 90 | 5 | 160 | 0.03 | 240 | 52 | 63 |
| 91 | 6 | 140 | 0.03 | 240 | 28 | 78 |
| 92 | 7 | 140 | 0.03 | 240 | 17 | 83 |
| 93 | 8 | 130 | 0.03 | 240 | 41 | 94 |

TABLE III-continued

| Example | Catalyst of Example | Temp | Press | GHSV | Conv | Select |
|---|---|---|---|---|---|---|
| 94 | 8 | 125 | 0.03 | 540 | 9 | 91 |
| 95 | 8 | 130 | 0.03 | 540 | 13 | 94 |
| 96 | 8 | 140 | 0.03 | 540 | 26 | 95 |
| 97 | 9 | 130 | 0.03 | 240 | 58 | 90 |
| 98 | 10 | 130 | 0.03 | 240 | 78 | 94 |
| 99 | 11 | 130 | 0.03 | 240 | 79 | 69 |
| 100 | 12 | 130 | 0.03 | 300 | 73 | 40 |
| 101 | 13 | 130 | 0.03 | 300 | 67 | 61 |
| 102 | 14 | 130 | 0.03 | 300 | 5 | 31 |
| 103 | 14 | 170 | 0.03 | 300 | 82 | 58 |
| 104 | 15 | 130 | 0.03 | 300 | 2 | 3 |
| 105 | 15 | 167 | 0.03 | 300 | 55 | 65 |
| 106 | 16 | 130 | 0.03 | 300 | 49 | 94 |
| 107 | 16 | 130 | 0.09 | 300 | 32 | 91 |
| 108 | 17 | 130 | 0.03 | 300 | 97 | 90 |
| 109 | 17 | 130 | 0.03 | 600 | 93 | 90 |
| 110 | 18 | 130 | 0.03 | 240 | 72 | 80 |
| 111 | 19 | 120 | 0.03 | 300 | 1 | 19 |
| 112 | 19 | 130 | 0.03 | 300 | 2 | 31 |
| 113 | 19 | 140 | 0.03 | 300 | 2 | 41 |
| 114 | 20 | 160 | 0.03 | 300 | 0.4 | 54 |

EXAMPLES 115-250

These examples demonstrate the favorable effect of using a Lewis acid co-catalyst in conjunction with a quaternary onium iodide compound as evidenced by an increase in the conversion of the 3,4-epoxy-1-butene reactant and/or increasing the selectivity to the desired 2,5-dihydrofuran. In Examples 137-140 the catalysts were subjected to a pretreatment in flowing helium at 140° C. for 30-60 minutes prior to starting the reactant feed.

TABLE IV

| Example | Catalyst of Example | Temp | Press | GHSV | Conv | Select |
|---|---|---|---|---|---|---|
| 115 | 2 | 125 | 0.17 | 75 | 64 | 91 |
| 116 | 2 | 125 | 0.17 | 190 | 38 | 94 |
| 117 | 2 | 130 | 0.17 | 75 | 83 | 93 |
| 118 | 2 | 130 | 0.17 | 190 | 50 | 93 |
| 119 | 2 | 130 | 0.17 | 750 | 14 | 92 |
| 120 | 21 | 120 | 0.09 | 300 | 0.2 | 36 |
| 121 | 21 | 130 | 0.09 | 300 | 0.3 | 45 |
| 122 | 21 | 140 | 0.09 | 300 | 0.6 | 67 |
| 123 | 22 | 130 | 0.09 | 300 | 28 | 93 |
| 124 | 23 | 130 | 0.09 | 300 | 15 | 87 |
| 125 | 24 | 120 | 0.09 | 300 | 5 | 99 |
| 126 | 24 | 130 | 0.09 | 300 | 7 | 99 |
| 127 | 24 | 140 | 0.09 | 300 | 8 | 98 |
| 128 | 25 | 120 | 0.09 | 300 | 7 | 94 |
| 129 | 25 | 130 | 0.09 | 300 | 12 | 93 |
| 130 | 26 | 120 | 0.09 | 300 | 10 | 96 |
| 131 | 27 | 130 | 0.09 | 300 | 6 | 75 |
| 132 | 28 | 130 | 0.09 | 300 | 8 | 93 |
| 133 | 29 | 130 | 0.09 | 300 | 15 | 98 |
| 134 | 30 | 130 | 0.09 | 300 | 2 | 95 |
| 135 | 31 | 130 | 0.09 | 300 | 6 | 71 |
| 136 | 32 | 130 | 0.09 | 300 | 8 | 95 |
| 137 | 33 | 130 | 0.03 | 300 | 86 | 90 |
| 138 | 34 | 130 | 0.03 | 300 | 84 | 85 |
| 139 | 35 | 130 | 0.03 | 300 | 56 | 72 |
| 140 | 36 | 130 | 0.03 | 300 | 73 | 85 |
| 141 | 37 | 130 | 0.03 | 300 | 62 | 89 |
| 142 | 38 | 130 | 0.03 | 300 | 90 | 82 |
| 143 | 39 | 130 | 0.03 | 300 | 92 | 62 |
| 144 | 40 | 120 | 0.09 | 300 | 7 | 99 |
| 145 | 40 | 140 | 0.09 | 300 | 8 | 98 |
| 146 | 41 | 120 | 0.09 | 300 | 13 | 94 |
| 147 | 42 | 120 | 0.09 | 300 | 10 | 96 |
| 148 | 42 | 130 | 0.09 | 300 | 15 | 65 |
| 149 | 43 | 130 | 0.09 | 300 | 12 | 97 |
| 150 | 44 | 130 | 0.09 | 300 | 16 | 95 |
| 151 | 44 | 130 | 0.13 | 300 | 15 | 95 |
| 152 | 45 | 120 | 0.09 | 60 | 79 | 98 |

TABLE IV-continued

| Example | Catalyst of Example | Temp | Press | GHSV | Conv | Select |
|---|---|---|---|---|---|---|
| 153 | 45 | 120 | 0.09 | 240 | 35 | 95 |
| 154 | 46 | 120 | 0.09 | 300 | 30 | 97 |
| 155 | 46 | 130 | 0.09 | 300 | 32 | 96 |
| 156 | 46 | 140 | 0.09 | 300 | 37 | 94 |
| 157 | 47 | 120 | 0.09 | 300 | 55 | 85 |
| 158 | 48 | 120 | 0.09 | 300 | 7 | 93 |
| 159 | 48 | 130 | 0.09 | 300 | 11 | 94 |
| 160 | 49 | 120 | 0.09 | 300 | 18 | 97 |
| 161 | 49 | 130 | 0.09 | 300 | 23 | 96 |
| 162 | 50 | 120 | 0.09 | 300 | 54 | 85 |
| 163 | 51 | 125 | 0.03 | 300 | 92 | 80 |
| 164 | 51 | 135 | 0.03 | 300 | 93 | 75 |
| 165 | 51 | 150 | 0.03 | 300 | 96 | 68 |
| 166 | 52 | 140 | 0.09 | 300 | 10 | 85 |
| 167 | 52 | 150 | 0.09 | 300 | 16 | 85 |
| 168 | 52 | 160 | 0.09 | 300 | 23 | 83 |
| 169 | 53 | 140 | 0.09 | 300 | 6 | 91 |
| 170 | 53 | 150 | 0.09 | 300 | 12 | 88 |
| 171 | 53 | 160 | 0.09 | 300 | 26 | 86 |
| 172 | 53 | 170 | 0.09 | 300 | 44 | 80 |
| 173 | 53 | 180 | 0.09 | 300 | 56 | 75 |
| 174 | 54 | 131 | 0.09 | 300 | 18 | 80 |
| 175 | 54 | 141 | 0.09 | 300 | 27 | 82 |
| 176 | 55 | 130 | 0.09 | 300 | 9 | 88 |
| 177 | 55 | 140 | 0.09 | 300 | 11 | 90 |
| 178 | 55 | 160 | 0.09 | 300 | 13 | 82 |
| 179 | 56 | 120 | 0.09 | 300 | 10 | 75 |
| 180 | 57 | 120 | 0.09 | 300 | 10 | 88 |
| 181 | 57 | 130 | 0.09 | 300 | 13 | 87 |
| 182 | 57 | 140 | 0.09 | 300 | 18 | 87 |
| 183 | 57 | 160 | 0.09 | 300 | 34 | 88 |
| 184 | 3 | 130 | 0.09 | 300 | 17 | 85 |
| 185 | 3 | 140 | 0.09 | 300 | 27 | 86 |
| 186 | 3 | 150 | 0.09 | 300 | 42 | 88 |
| 187 | 3 | 160 | 0.09 | 300 | 50 | 86 |
| 188 | 3 | 170 | 0.09 | 300 | 57 | 85 |
| 189 | 58 | 120 | 0.09 | 300 | 18 | 93 |
| 190 | 58 | 130 | 0.09 | 300 | 26 | 94 |
| 191 | 58 | 140 | 0.09 | 300 | 30 | 94 |
| 192 | 58 | 150 | 0.09 | 300 | 43 | 93 |
| 193 | 59 | 130 | 0.09 | 60 | 38 | 89 |
| 194 | 59 | 140 | 0.09 | 60 | 84 | 89 |
| 195 | 59 | 140 | 0.09 | 120 | 60 | 91 |
| 196 | 60 | 130 | 0.09 | 300 | 35 | 95 |
| 197 | 60 | 160 | 0.09 | 300 | 55 | 92 |
| 198 | 61 | 140 | 0.09 | 300 | 26 | 90 |
| 199 | 61 | 160 | 0.09 | 300 | 41 | 90 |
| 200 | 62 | 140 | 0.09 | 300 | 30 | 92 |
| 201 | 62 | 160 | 0.09 | 300 | 45 | 90 |
| 202 | 63 | 130 | 0.09 | 300 | 37 | 94 |
| 203 | 64 | 130 | 0.09 | 300 | 27 | 90 |
| 204 | 65 | 140 | 0.09 | 300 | 24 | 92 |
| 205 | 66 | 140 | 0.09 | 300 | 26 | 79 |
| 206 | 67 | 130 | 0.09 | 300 | 9 | 61 |
| 207 | 67 | 170 | 0.09 | 300 | 15 | 75 |
| 208 | 68 | 140 | 0.09 | 300 | 11 | 62 |
| 209 | 69 | 160 | 0.09 | 300 | 12 | 71 |
| 210 | 69 | 180 | 0.09 | 300 | 68 | 95 |
| 211 | 70 | 160 | 0.09 | 300 | 64 | 93 |
| 212 | 71 | 140 | 0.09 | 300 | 34 | 95 |
| 213 | 71 | 160 | 0.09 | 300 | 50 | 94 |
| 214 | 72 | 140 | 0.09 | 300 | 12 | 80 |
| 215 | 72 | 160 | 0.09 | 300 | 28 | 85 |
| 216 | 73 | 125 | 0.09 | 300 | 21 | 95 |
| 217 | 73 | 130 | 0.09 | 300 | 37 | 94 |
| 218 | 74 | 130 | 0.03 | 540 | 5 | 81 |
| 219 | 74 | 150 | 0.03 | 540 | 20 | 80 |
| 220 | 75 | 130 | 0.09 | 540 | 3 | 80 |
| 221 | 75 | 130 | 0.03 | 540 | 7 | 80 |
| 222 | 75 | 160 | 0.03 | 540 | 29 | 73 |
| 223 | 76 | 140 | 0.03 | 240 | 15 | 50 |
| 224 | 76 | 160 | 0.03 | 240 | 50 | 49 |
| 225 | 77 | 140 | 0.03 | 540 | 10 | 35 |
| 226 | 77 | 160 | 0.03 | 540 | 15 | 41 |
| 227 | 77 | 170 | 0.03 | 240 | 59 | 61 |
| 228 | 78 | 125 | 0.17 | 150 | 65 | 51 |
| 229 | 79 | 125 | 0.09 | 75 | 55 | 86 |
| 230 | 79 | 125 | 0.09 | 190 | 29 | 84 |
| 231 | 80 | 125 | 0.17 | 90 | 68 | 93 |
| 232 | 80 | 125 | 0.17 | 250 | 34 | 92 |

TABLE IV-continued

| Example | Catalyst of Example | Temp | Press | GHSV | Conv | Select |
|---|---|---|---|---|---|---|
| 233 | 80 | 125 | 0.17 | 500 | 16 | 93 |
| 234 | 80 | 125 | 0.17 | 1000 | 8 | 93 |
| 235 | 80 | 130 | 0.17 | 1000 | 18 | 93 |
| 236 | 81 | 125 | 0.17 | 250 | 8 | 78 |
| 237 | 81 | 130 | 0.17 | 250 | 13 | 85 |
| 238 | 82 | 130 | 0.03 | 60 | 11 | 64 |
| 239 | 82 | 135 | 0.03 | 60 | 25 | 77 |
| 240 | 82 | 140 | 0.03 | 60 | 48 | 83 |
| 241 | 83 | 130 | 0.03 | 160 | 32 | 63 |
| 242 | 83 | 135 | 0.03 | 160 | 36 | 64 |
| 243 | 83 | 140 | 0.03 | 160 | 53 | 67 |
| 244 | 84 | 150 | 0.09 | 600 | 8 | 81 |
| 245 | 84 | 160 | 0.09 | 600 | 10 | 78 |
| 246 | 85 | 130 | 0.09 | 300 | 14 | 98 |
| 247 | 85 | 130 | 0.09 | 600 | 8 | 98 |
| 248 | 85 | 140 | 0.09 | 300 | 22 | 98 |
| 249 | 86 | 130 | 0.09 | 300 | 13 | 99 |
| 250 | 86 | 140 | 0.09 | 300 | 26 | 98 |

EXAMPLE 251-255

Using the catalyst of Example 2 and the isomerization procedure described hereinabove, two other $\gamma,\delta$-epoxyalkenes and a $\gamma,\delta$-epoxycycloalkene were isomerized to 2,5-dihydrofuran compounds. The reactants used and the desired dihydrofuran product obtained were:

| Example | Reactant | Dihydrofuran Product |
|---|---|---|
| 251,252 | 2-Methyl-3,4-epoxy-1-butene | 3-methyl-2,5-dihydrofuran |
| 253,254 | 2,3-Dimethyl-3,4-epoxy-1-butene | 3,4-Dimethyl-2,5-dihydrofuran |
| 255 | 3,4-epoxycyclooctene | 9-oxa-bicyclo[4.2.1]-non-7-ene |

The results obtained are set forth in Table V wherein Conv is the mole percent of moles of reactant converted to other products per moles of reactant fed and Select is the percent moles of reactant converted to the desired 2,5-dihydrofuran product based on the moles of reactant converted.

TABLE V

| Example | Temp | Press | GHSV | Conv | Select |
|---|---|---|---|---|---|
| 251 | 126 | 0.04 | 60 | 65 | 66 |
| 252 | 126 | 0.04 | 120 | 46 | 67 |
| 253 | 127 | 0.03 | 60 | 51 | 81 |
| 254 | 127 | 0.05 | 60 | 46 | 81 |
| 255 | 130 | 0.01 | 60 | 61 | 90 |

EXAMPLE 256-300

These examples demonstrate the use of the unsupported catalyst systems of this invention in the isomerization of 3,4-epoxy-1-butene to 2,5-dihydrofuran according to the general procedure described relative to the preceding isomerization examples. Because the catalyst can exist in a substantially molten state if the process is operated above the melting point of the quaternary onium iodide salt, the reactor was operated in an upward flow mode whereby the gaseous feed entered below the catalyst bed and passed through a gas dispersion frit upon which the unsupported catalyst system was supported to maintain the catalyst in the proper position in the reactor. Alternatively, the catalyst was maintained in a vessel with a closed bottom into which the feed gas was added below the level of the substantially molten catalyst by means of a gas dispersion apparatus. In both reactor configurations, the gaseous reactor effluent comprising unreacted feed and product exited the top of the reactor into the downstream assembly described hereinabove.

In the examples utilizing an unsupported catalyst system, the catalyst components were heated in an inert gas flow, typically 100 mL (STP) per minute of helium, until both catalyst components existed in a molten state. At this point, a partial pressure of 3,4-epoxy-1-butene was introduced into the carrier gas stream and the catalytic reaction as initiated. Typical molar concentrations of 3,4-epoxy-1-butene in the carrier gas varied from 3 to 25%, with 9 to 10% being the most commonly used feed concentration.

The unsupported catalyst systems listed below were prepared by physically and intimately mixing the components while in the solid state and were used in Examples 256-326. For catalyst components which were potentially air sensitive, care was taken to prevent contact with air while loading into the catalytic reactor.

| | |
|---|---|
| (i) | Tetradodecylammonium iodide (1.20 g) and zinc iodide (24.0 mg) |
| (ii) | Triphenyl(hexyl)phosphonium iodide (1.00 g) and zinc iodide (5.0 mg) |
| (iii) | Triphenyl(hexyl)phosphonium iodide (0.50 g), tris-(2,4,6-trimethylphenyl)(hexyl)phosphonium iodide (0.50 g) and zinc iodide (5.0 mg) |
| (iv) | Tetradodecylammonium iodide (20.0 g) and tributyltin iodide (0.52 g) |
| (v) | Tetradodecylammonium iodide (10.0 g) and dibutyltin diiodide (0.30 g) |
| (vi) | Tetradodecylammonium iodide (10.0 g) and triphenyltin iodide (0.29 g) |
| (vii) | Triphenyl(hexyl)phosphonium iodide (10.0 g) and tributyltin iodide (0.07 g) |
| (viii) | Triphenyl(hexyl)phosphonium iodide (10.0 g) and dibutyltin diiodide (0.21 g) |
| (ix) | Tetradodecylammonium iodide (10.0 g) and trioctyltin iodide (0.36 g) |
| (x) | Triphenyl(hexyl)phosphonium iodide (10.0 g) and trioctyltin iodide (0.25 g) |
| (xi) | Tetrabutylarsonium iodide (8.00 g) and trioctyltin iodide (0.54 g) |
| (xii) | Tetraoctylarsonium iodide (8.00 g) and trioctyltin iodide (0.38 g) |
| (xiii) | Triphenyl(hexyl)phosphonium iodide (11.6 g) and triphenyltin iodide (0.24 g) |
| (xiv) | Triphenyl(hexyl)phosphonium iodide (11.6 g) and triphenyltin iodide (0.59 g) |
| (xv) | Triphenyl(hexyl)phosphonium iodide (11.6 g) and triphenyltin iodide (2.33 g) |
| (xvi) | Triphenyl(hexyl)phosphonium iodide (6.0 g) and triphenyltin iodide (6.0 g) |
| (xvii) | Triphenyl(hexyl)phosphonium iodide (2.0 g) and triphenyltin iodide (10.0 g) |
| (xviii) | Triphenyl(hexyl)phosphonium iodide (0.60 g) and triphenyltin iodide (11.4 g) |
| (xix) | Triphenyl(hexyl)phosphonium iodide (0.10 g) and triphenyltin iodide (10.0 g) |
| (xx) | Triphenyl(hexyl)phosphonium iodide (2.0 g) and tricyclohexyltin iodide (10.4 g) |
| (xxi) | Triphenyl(hexyl)phosphonium iodide (2.0 g) and tribenzyltin iodide (10.9 g) |

The ratio of zinc oxide to quaternary onium iodide compound(s) in each of catalyst systems (i) and (ii) is the same as the analogous ratio for the supported catalysts of Examples 22 and 59, respectively.

TABLE VI

| Example | Catalyst System | Temp | Press | GHSV | Conv | Select |
|---|---|---|---|---|---|---|
| 256 | (i) | 110 | 0.09 | 500 | 17 | 77 |

TABLE VI-continued

| Example | Catalyst System | Temp | Press | GHSV | Conv | Select |
|---|---|---|---|---|---|---|
| 257 | (i) | 120 | 0.09 | 500 | 44 | 90 |
| 258 | (i) | 130 | 0.09 | 500 | 60 | 93 |
| 259 | (i) | 140 | 0.09 | 500 | 88 | 94 |
| 260 | (ii) | 140 | 0.09 | 1200 | 25 | 91 |
| 261 | (ii) | 150 | 0.09 | 1200 | 30 | 90 |
| 262 | (ii) | 160 | 0.09 | 1200 | 36 | 87 |
| 263 | (ii) | 160 | 0.09 | 2400 | 18 | 91 |
| 264 | (iii) | 130 | 0.09 | 600 | 17 | 82 |
| 265 | (iii) | 140 | 0.09 | 600 | 43 | 92 |
| 266 | (iii) | 160 | 0.09 | 600 | 59 | 86 |
| 267 | (iii) | 180 | 0.09 | 600 | 72 | 80 |
| 268 | (iv) | 130 | 0.09 | 120 | 95 | 95 |
| 269 | (iv) | 130 | 0.09 | 300 | 75 | 98 |
| 270 | (iv) | 130 | 0.09 | 600 | 60 | 99 |
| 271 | (v) | 130 | 0.09 | 240 | 96 | 96 |
| 272 | (v) | 130 | 0.09 | 600 | 83 | 97 |
| 273 | (v) | 130 | 0.09 | 1200 | 34 | 96 |
| 274 | (vi) | 130 | 0.09 | 240 | 98 | 98 |
| 275 | (vi) | 130 | 0.09 | 600 | 78 | 99 |
| 276 | (vi) | 130 | 0.09 | 1200 | 55 | 99 |
| 277 | (vi) | 140 | 0.09 | 240 | 98 | 95 |
| 278 | (vi) | 140 | 0.09 | 600 | 89 | 98 |
| 279 | (vi) | 140 | 0.09 | 1200 | 75 | 98 |
| 280 | (vii) | 140 | 0.09 | 120 | 68 | 81 |
| 281 | (vii) | 140 | 0.09 | 600 | 24 | 88 |
| 282 | (viii) | 130 | 0.09 | 240 | 71 | 93 |
| 283 | (viii) | 130 | 0.09 | 600 | 37 | 94 |
| 284 | (viii) | 130 | 0.09 | 1200 | 21 | 94 |
| 285 | (viii) | 140 | 0.09 | 240 | 80 | 90 |
| 286 | (viii) | 140 | 0.09 | 1200 | 22 | 92 |
| 287 | (ix) | 130 | 0.09 | 600 | 40 | 99 |
| 288 | (ix) | 130 | 0.09 | 1200 | 20 | 98 |
| 289 | (ix) | 140 | 0.09 | 600 | 68 | 98 |
| 290 | (ix) | 140 | 0.09 | 1200 | 46 | 99 |
| 291 | (ix) | 140 | 0.09 | 240 | 89 | 96 |
| 292 | (x) | 130 | 0.09 | 300 | 53 | 90 |
| 293 | (x) | 130 | 0.09 | 600 | 30 | 92 |
| 294 | (x) | 130 | 0.09 | 1200 | 14 | 94 |
| 295 | (x) | 140 | 0.09 | 600 | 43 | 91 |
| 296 | (x) | 140 | 0.09 | 1200 | 20 | 93 |
| 297 | (xi) | 130 | 0.09 | 300 | 80 | 97 |
| 298 | (xi) | 130 | 0.09 | 600 | 65 | 98 |
| 299 | (xii) | 130 | 0.09 | 300 | 28 | 98 |
| 300 | (xii) | 130 | 0.09 | 600 | 18 | 98 |
| 301 | (xiii) | 130 | 0.10 | 300 | 38 | 93 |
| 302 | (xiii) | 130 | 0.10 | 600 | 22 | 94 |
| 303 | (xiv) | 130 | 0.10 | 300 | 80 | 93 |
| 304 | (xiv) | 130 | 0.10 | 600 | 67 | 93 |
| 305 | (xiv) | 140 | 0.10 | 300 | 88 | 92 |
| 306 | (xiv) | 140 | 0.10 | 600 | 74 | 92 |
| 307 | (xv) | 130 | 0.10 | 300 | 87 | 95 |
| 308 | (xv) | 130 | 0.10 | 600 | 69 | 95 |
| 309 | (xv) | 140 | 0.10 | 300 | 91 | 95 |
| 310 | (xv) | 140 | 0.10 | 600 | 71 | 94 |
| 311 | (xv) | 140 | 0.25 | 600 | 64 | 95 |
| 312 | (xvi) | 130 | 0.10 | 300 | 100 | 97 |
| 313 | (xvi) | 130 | 0.10 | 600 | 99 | 97 |
| 314 | (xvii) | 130 | 0.10 | 300 | 100 | 98 |
| 315 | (xvii) | 130 | 0.10 | 600 | 100 | 98 |
| 316 | (xvii) | 130 | 0.25 | 300 | 99 | 97 |
| 317 | (xvii) | 130 | 0.25 | 1000 | 91 | 97 |
| 318 | (xviii) | 130 | 0.10 | 300 | 80 | 97 |
| 319 | (xviii) | 130 | 0.10 | 600 | 67 | 97 |
| 320 | (xviii) | 130 | 0.25 | 600 | 62 | 97 |
| 321 | (xix) | 130 | 0.10 | 300 | 68 | 96 |
| 322 | (xix) | 130 | 0.10 | 600 | 56 | 96 |
| 323 | (xx) | 130 | 0.10 | 300 | 14 | 96 |
| 324 | (xx) | 130 | 0.10 | 600 | 9 | 96 |
| 325 | (xxi) | 130 | 0.10 | 300 | 70 | 85 |
| 326 | (xxi) | 130 | 0.10 | 600 | 54 | 81 |

EXAMPLES 327-331

The following examples illustrate the isomerization of 3,4-epoxy-1-butene to 2,5-dihydrofuran using the catalyst solutions described hereinabove. The gas chromatographic (GC) analyses were performed on a Hewlett-Packard 5890A gas chromatograph with a DB5-30W capillary column; temperature program 35° C. (4.5 minutes), 20° C./minute to 260° C. (hold 6 minutes). 1H NMR analyses were performed on a Varian Gemini 300 spectrometer (300 MHz) using CDCl3 as solvent and tetramethylsilane as internal standard.

EXAMPLE 327

To a nitrogen-purged, 500-mL, four-neck flask equipped with a thermometer, addition funnel, condenser, magnetic stirrer, and heating mantle was charged 170.57 g of p-xylene, 21.62 g (0.05185 moles) of tributyltin iodide, and 39.76 g (0.07394 moles) of tetraheptylammonium iodide. The mixture was heated to 109° C. and 34.04 g (0.4857 moles) of 3,4-epoxy-1-butene was added dropwise over 15 minutes at 109°-117° C. Thirty minutes after the addition the reaction was complete as shown by GC. After cooling, the condenser was replaced with a fractional distillation apparatus and the mixture distilled. A 36.81 g fraction boiling at 62°-134° C. was collected which had the following GC assay: 0.11% furan, 0.32% 3,4-epoxy-1-butene, 1.32% crotonaldehyde, 88.86% 2.5-dihydrofuran, and 9.39% p-xylene. The yield of 2,5-dihydrofuran was 96.1%.

EXAMPLE 328

To a nitrogen-purged, 500-mL, four-neck flask equipped with a thermometer, addition funnel, condenser, magnetic stirrer, and heating mantle was charged 213.58 g of p-xylene, 28.81 g (0.06910 moles) of tributyltin iodide, and 32.27 g (0.05785 moles) of dodecyltriphenylphosphonium iodide. The mixture was heated to 110° C. and 34.66 g (0.4945 moles) of 3,4-epoxy-1-butene was added dropwise over 18 minutes at 110°-119° C. Thirty-five minutes after the addition the reaction was complete as shown by GC. After cooling, the condenser was replaced with a fractional distillation apparatus and the mixture distilled. A 35.22 g fraction boiling at 59°-105° C. was collected which had the following GC assay: 0.2% 3,4-epoxy-1.butene, 0.4% crotonaldehyde, 87.2% 2.5-dihydrofuran, and 8.6% p-xylene. The yield of 2,5-dihydrofuran was 87.2%.

EXAMPLE 329

The process of this invention may be operated continuously as shown by this example. The continuous reaction system consists of a heated, plug-flow reactor (465 mL, U-tube of Pyrex glass) into which the 3,4-epoxy-1-butene and recirculated catalyst solution is pumped. After a residence time in the reactor at the rearrangement temperature the homogeneous reaction stream feeds into the center of a fractional distillation column. The volatile materials are condensed with a water-cooled condenser and collected in the receiver. The stripped catalyst solution from the distillation pot is returned to the reactor along with fresh 3,4-epoxy-1-butene. This system was charged with a solution of 41.7 g (0.100 mole) of tributyltin iodide, 47.4 g (0.123 mole) of tetrabutylphosphonium iodide, and 525 mL of o-dichlorobenzene. The reactor tube was heated to 130° C. and the distillation pot was heated to reflux (pot temperature 205°-213° C.). The catalyst solution was recycled at a rate of 30.2 mL/minute and 3,4-epoxy-1-butene was fed at a rate of 1.2 g/minute giving a total flow rate through the reactor of 32 mL/minute for a reactor residence time of 15 minutes. A total of 400.2 g (5.710 mole) of 3,4-epoxy-1.butene was fed to the system and 371.5 g of distillate (bp 66° C.) was obtained. The distillate had a GC analysis of 92.7% 2,5-dihydrofuran, 2.95% of 3,4-epoxy-1-butene, and 0.48% of crotonaldehyde. The assay yield of 2,5dihydrofuran was 86.1%.

EXAMPLE 330

To a nitrogen-purged, 100-mL, three-neck flask equipped with a thermometer, condenser, magnetic stirrer, and heating mantle was charged 50 mL of p-xylene, 4.35 g (0.0104 moles) of tributyltin iodide, 6.49 g (0.0121 moles) of tetraheptylammonium iodide and 10.28 g (0.1222 moles) of 3,4-epoxy-3-methyl-1-butene. The mixture was heated to reflux (119° C.). After two hours the reaction was complete as judged by GC. After cooling, the condenser was replaced with a distillation head and the mixture distilled. A 17.26 g fraction boiling at 82°-120° C. was collected which had the following NMR weight-percent assay: 70.3% p-xylene, 24.3% 3-methyl-2,5.dihydrofuran, and 5.5% 2-methyl-2butenal. The yield of 3-methyl-2,5-dihydrofuran was 40.8% and the yield of 2-methyl-2-butenal was 9.2%.

EXAMPLE 331

To a nitrogen-purged, 25-mL, three-neck flask equipped with a thermometer, condenser, magnetic stirrer, and heating mantle was charged 12.5 mL of p-xylene, 0.94 g (0.023 moles) of tributyltin iodide, 1.69 g (0.00314 moles) of tetraheptylammonium iodide and 3.10 g (0.0235 moles) of 3,4-epoxycyclooctene (94.1%). The mixture was heated to reflux (125° C.). After five hours the reaction was complete as shown by GC. After cooling, the tetraheptylammonium iodide solids were filtered then the filtrate was filtered through a small pad of silica gel and rinsed with p-xylene. The solvent was distilled off at atmospheric pressure leaving 2.43 g of an oil which had the following NMR weight-percent assay: 42.8% 9-oxabicyclo[4.2.1]non-7-ene and 57.2% p-xylene. The yield of 9-oxabicyclo[4.2.1]non-7-ene was 35.7%.

The invention has been described in detail with particular reference to preferred embodiments thereof, but it will be understood that variations and modifications can be effected within the spirit and scope of the invention.

We claim:

1. Process for the isomerization of a $\gamma,\delta$-epoxyalkene or a $\gamma,\delta$-epoxycycloalkene to the corresponding 2,5-dihydrofuran which comprises contacting a $\gamma,\delta$-epoxyalkene or a $\gamma,\delta$-epoxycycloalkene in the gas phase with a catalytic amount of a quaternary organic onium compound containing at least 6 carbon atoms.

2. Process according to claim 1 wherein the quaternary organic onium compound has the formula

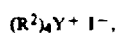

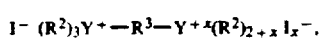

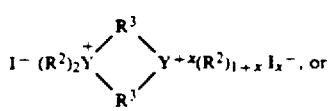

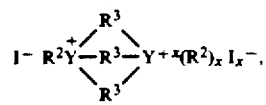

wherein
each $R^2$ independently is selected from hydrogen, alkyl or substituted alkyl moieties having up to about carbon atoms, cycloalkyl or substituted cycloalkyl having about 5 to 20 carbon atoms or aryl or substituted aryl having about 6 to 20 carbon atoms; ferrocenyl; or when Y is P, each $R^2$ also may be selected from alkoxy of up to about 20 carbon atoms, cycloalkoxy of about 5 to carbon atoms, aryloxy of 6 to 10 carbon atoms or halogen;
two or three $R^2$ substituents collectively may represent joined hydrocarbylene groups which form a mono- or poly-cyclic ring with the Y atom to which they are bonded;
each $R^3$ is independently selected from hydrocarbylene moieties or substituted hydrocarbylene moieties;
x is 0 or 1, and
Y is N, P or As; provided that the quaternary onium iodide contains at least 6 carbon atoms.

3. Process according to claim 2 wherein the process is carried out at a temperature of about 60° to 225° C. and a pressure of about 1.02 to 70 bar.

4. Process for the isomerization of a $\gamma,\delta$-epoxyalkene or a $\gamma,\delta$-epoxycycloalkene having the formula

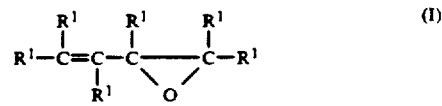

to the corresponding 2,5-dihydrofuran having the formula

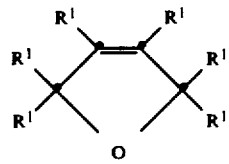

wherein each $R^1$ is hydrogen or up to 2 $R^1$ substituents each may be alkyl of up to about 8 carbon or collectively straight or branched chain alkylene of up to about 8 carbon atoms, which comprises contacting the $\gamma,\delta$-epoxyalkene or a $\gamma,\delta$-epoxycycloalkene in the gas phase at a temperature of about 60° to 225° C. and a pressure of about 1.02 to 70 bar with a catalytic amount of a supported quaternary organic onium iodide compound containing at least 6 carbon atoms and having a melting temperature not exceeding about 225° C. and the formula

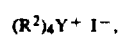

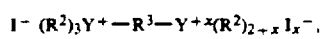

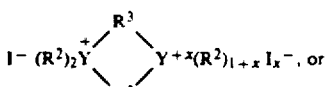

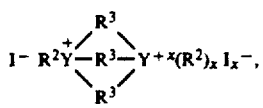

wherein
- each $R^2$ is independently selected from hydrogen, alkyl or substituted alkyl moieties having up to about carbon atoms, cycloalkyl or substituted cycloalkyl having about 5 to 20 carbon atoms, aryl or substituted aryl having about 6 to 20 carbon atoms; ferrocenyl; or when Y is P, each $R^2$ also may be selected from alkoxy of up to about 20 carbon atoms, cycloalkoxy of about 5 to carbon atoms, aryloxy of 6 to 10 carbon atoms or halogen;
- two or three $R^2$ substituents collectively may represent joined hydrocarbylene groups which form a mono- or poly-cyclic ring with the Y atom to which they are bonded;
- each $R^3$ is independently selected from hydrocarbylene moieties or substituted hydrocarbylene moieties;
- x is 0 or 1, and
- Y is N, P or As.

5. Process for the isomerization of a γ,δ-epoxyalkene or a γ,δ-epoxycycloalkene to the corresponding 2,5-dihydrofuran which comprises contacting a γ,δ-epoxyalkene or a γ,δ-epoxycycloalkene in the gas phase with a catalytic amount of a supported catalyst comprising (1) about 0.1 to 30 weight percent of at least one quaternary organic onium iodide compound having at least 6 carbon atoms calculated as weight iodide and based on the total weight of the catalyst and (2) about 0.01 to 30 weight percent, based on the total weight of the catalyst, of a Lewis acid and (3) an essentially nonacidic catalyst support material.

6. Process for the isomerization of a γ,δ-epoxyalkene or a γ,δ-epoxycycloalkene having the formula

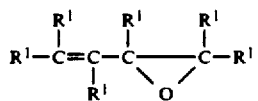

to the corresponding 2,5-dihydrofuran having the formula

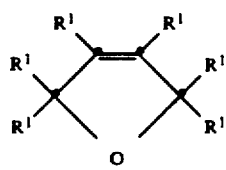

wherein each $R^1$ is hydrogen or up to 2 $R^1$ substituents each may be alkyl of up to about 8 carbon or collectively straight or branched chain alkylene of up to about 8 carbon atoms, which comprises contacting the γ,δ-epoxyalkene or a γ,δ-epoxycycloalkene in the gas phase at a temperature of about 60° to 225° C. and a pressure of about 1.02 to 70 bar with a catalytic amount of a supported catalyst comprising (1) at least one quaternary organic onium iodide compound containing at least 6 carbon atoms and having a melting temperature not exceeding about 225° C. and the formula

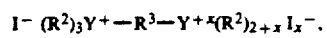
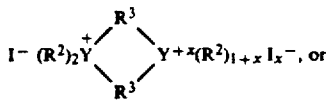
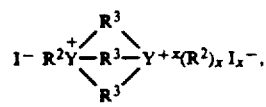

wherein
- each $R^2$ is independently selected from hydrogen, alkyl or substituted alkyl moieties having up to about carbon atoms, cycloalkyl or substituted cycloalkyl having about 5 to 20 carbon atoms, aryl or substituted aryl having about 6 to 20 carbon atoms; ferrocenyl; or when Y is P, each $R^2$ also may be selected from alkoxy of up to about 20 carbon atoms, cycloalkoxy of about 5 to carbon atoms, aryloxy of 6 to 10 carbon atoms or halogen;
- two or three $R^2$ substituents collectively may represent joined hydrocarbylene groups which form a mono- or poly-cyclic ring with the Y atom to which they are bonded;
- each $R^3$ is independently selected from hydrocarbylene moieties or substituted hydrocarbylene moieties;
- x is 0 or 1, and
- Y is N, P or As;

wherein the quaternary iodide compound, calculated as weight iodide, constitutes 0.1 to 30 weight percent of the total weight of the catalyst; (2) about 0.01 to 10 weight percent, based on the total weight of the catalyst, of an inorganic Lewis acid and (3) an essentially non-acidic catalyst support material.

7. Process according to claim 6 wherein the catalyst comprises (1) about 0.5 to 20 weight percent, calculated as weight iodide and based on the total weight of the catalyst of at least one quaternary ammonium or phosphonium iodide, (2) about 0.02 to 5.0 weight percent, based on the total weight of the catalyst, of titanium (IV) iodide, zirconium (IV) iodide, zinc iodide or tin (II) iodide and (3) an essentially non-acidic catalyst support material.

8. Process for the isomerization of a γ,δ-epoxyalkene or a γ,δ-epoxycycloalkene having the formula

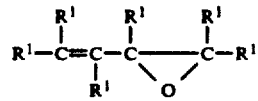

to the corresponding 2,5-dihydrofuran having the formula

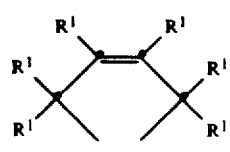

wherein each R¹ is hydrogen or up to 2 R¹ substituents each may be alkyl of up to about 8 carbon or collectively straight or branched chain alkylene of up to about 8 carbon atoms, which comprises contacting the γ,δ-epoxyalkene or a γ,δ-epoxycycloalkene in the gas phase at a temperature of about 60° to 225° C. and a pressure of about 1.02 to 70 bar with a catalytic amount of a catalyst comprising a melt of (1) at least one quaternary organic onium iodide compound containing at least 6 carbon atoms and having a melting temperature not exceeding about 225° C. and the formula

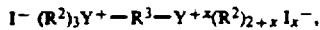

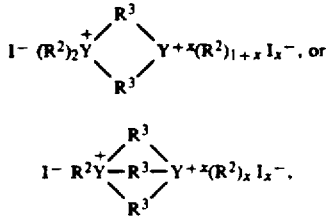

wherein
each R² is independently selected from hydrogen, alkyl or substituted alkyl moieties having up to about 20 carbon atoms, cycloalkyl or substituted cycloalkyl having about 5 to 20 carbon atoms, aryl or substituted aryl having about 6 to 20 carbon atoms; ferrocenyl; or when Y is P, each R² also may be selected from alkoxy of up to about 20 carbon atoms, cycloalkoxy of about 5 to 20 carbon atoms, aryloxy of 6 to 10 carbon atoms or halogen; two or three R² substituents collectively may represent joined hydrocarbylene groups which form a mono- or poly-cyclic ring with the Y atom to which they are bonded;
each R³ is independently selected from hydrocarbylene moieties or substituted hydrocarbylene moieties;
x is 0 or 1, and
Y is N or P; and
(2) titanium (IV) iodide, zirconium (IV) iodide, zinc iodide or tin (II) iodide; wherein the weight ratio of (1):(2) is about 200:1 to 5:1.

9. Process for the isomerization of 3,4-epoxy-1-butene to 2,5-dihydrofuran which comprises contacting the 3,4-epoxy-1-butene in the gas phase at a temperature of about 100° to 200° C. and a pressure of about 1.1 to 20 bar with a catalytic amount of a catalyst comprising one or more quaternary ammonium iodides having the formula

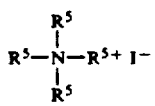

wherein each R⁵ substituent independently is selected from alkyl of up to 20 carbon atoms, two R⁵ substituents collectively may represent alkylene of 4 to 6 carbon atoms or alkylene of 4 to 6 carbon atoms substituted with lower alkyl and the quaternary ammonium iodide contains about 16 to 60 carbon atoms.

10. Process according to claim 9 wherein the catalyst is a supported catalyst comprising (1) about 0.5 to 20 weight percent, calculated as weight iodide and based on the total weight of the catalyst, of one or more quaternary ammonium iodides having the formula

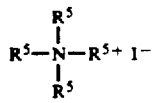

wherein each R⁵ substituent is independently selected from alkyl of up to 20 carbon atoms and the quaternary ammonium iodide contains about 16 to 60 carbon atoms, (2) about 0.02 to 5.0 weight percent, based on the total weight of the catalyst of zinc iodide or tin (II) iodide and (3) an essentially non-acidic catalyst support.

11. A process according to claim 10 wherein the catalyst support material is zinc oxide, silica or alumina.

12. Process according to claim 9 wherein the catalyst comprises a melt of (1) one or more quaternary ammonium iodides having the formula

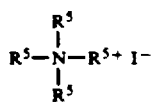

wherein each R⁵ substituent is independently selected from alkyl of up to 20 carbon atoms and the quaternary ammonium iodide contains about 16 to 60 carbon atoms and (2) zinc iodide or tin (II) iodide; wherein the weight ratio of (1):(2) is about 200:1 to 5:1.

13. Process for the isomerization of 3,4-epoxy-1-butene to 2,5-dihydrofuran which comprises contacting the 3,4-epoxy-1-butene in the gas phase at a temperature of about 100° to 200° C. and a pressure of about 1.1 to 20 bar with a catalytic amount of a catalyst comprising one or more quaternary ammonium iodides having the formula

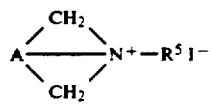

wherein R⁵ is alkyl of up to about 20 carbon atoms and A is the residue of an azabicycloalkane or diazabicycloalkane having 6 to 12 ring carbon atoms.

14. Process according to claim 13 wherein the catalyst is a supported catalyst comprising (1) about 0.5 to 20 weight percent, calculated as weight iodide and based on the total weight of the catalyst, of one or more quaternary ammonium iodides having the formula

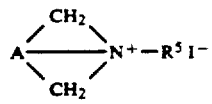

wherein R⁵ is alkyl of up to about 20 carbon atoms and A is the residue of an azabicycloalkane or diazabicycloalkane having 6 to 12 ring carbon atoms, (2) about 0.02 to 5.0 weight percent, based on the total weight of the catalyst of zinc iodide or tin (II) iodide and (3) an essentially non-acidic catalyst support.

15. A process according to claim 14 wherein the catalyst support material is zinc oxide, silica or alumina.

16. Process according to claim 13 wherein the catalyst comprises a melt of (1) of one or more quaternary ammonium iodides having the formula

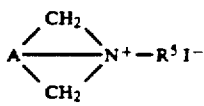

wherein $R^5$ is alkyl of up to about 20 carbon atoms and A is the residue of an azabicycloalkane or diazabicycloalkane having 6 to 12 ring carbon atoms and (2) zinc iodide or tin (II) iodide; wherein the weight ratio of (1):(2) is about 200:1 to 5:1.

17. Process for the isomerization of 3,4-epoxy-1-butene to 2,5-dihydrofuran which comprises contacting the 3,4-epoxy-1-butene in the gas phase at a temperature of about 100° to 200° C. and a pressure of about 1.1 to 20 bar with a catalytic amount of a catalyst comprising one or more quaternary phosphonium iodides having the formula

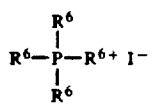

wherein each $R^6$ substituent is independently selected from alkyl of up to 20 carbon atoms benzyl, phenyl or phenyl substituted with up to 3 substituents selected from lower alkyl, lower alkoxy and halogen and the phosphonium iodide contains about 16 to 60 carbon atoms.

18. Process according to claim 17 wherein the catalyst is a supported catalyst comprising (1) about 0.5 to 20 weight percent, calculated as weight iodide and based on the total weight of the catalyst, of one or more quaternary phosphonium iodides having the formula

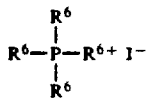

wherein each $R^6$ substituent is independently selected from alkyl of up to 20 carbon atoms, benzyl, phenyl or phenyl substituted with up to 3 substituents selected from lower alkyl, lower alkoxy and halogen and the phosphonium iodide contains about 16 to 60 carbon atoms, (2) about 0.02 to 5.0 weight percent, based on the total weight of the catalyst of zinc iodide or tin (II) iodide and (3) an essentially non-acidic catalyst support.

19. A process according to claim 18 wherein the catalyst support material is zinc oxide, silica or alumina.

20. Process according to claim 17 wherein the catalyst comprises a melt of (1) one or more quaternary phosphonium iodides having the formula

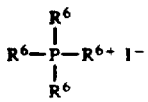

wherein and each $R^6$ substituent is independently selected from alkyl of up to 20 carbon atoms, benzyl, phenyl or phenyl substituted with up to 3 substituents selected from lower alkyl, lower alkoxy and halogen and the phosphonium iodide contains about 16 to 60 carbon atoms and (2) zinc iodide or tin (II) iodide; wherein the weight ratio of (1):(2) is about 200:1 to 5:1.

21. Process for the isomerization of a γ,δ-epoxyalkene or a γ,δ-epoxycycloalkene to the corresponding 2,5-dihydrofuran which comprises contacting a γ,δ-epoxyalkene or a γ,δ-epoxycycloalkene in the gas phase with a catalytic amount of a catalyst comprising (1) at least one quaternary organic onium iodide compound having at least 6 carbon atoms and (2) an organotin (IV) compound or organostibonium compound.

22. Process according to claim 21 for the isomerization of a γ,δ-epoxyalkene or a γ,δ-epoxycycloalkene having the formula

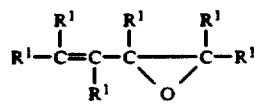

to the corresponding 2,5-dihydrofuran having the formula

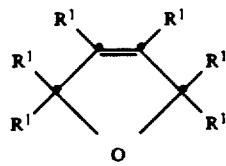

wherein each $R^1$ is hydrogen or up to 2 $R^1$ substituents each may be alkyl of up to about 8 carbon or collectively straight or branched chain alkylene of up to about carbon atoms, which comprises contacting the γ,δ-epoxyalkene or a γ,δ-epoxycycloalkene in the gas phase at a temperature of about 60° to 225° C. and a pressure of about 1.02 to 70 bar with a catalytic amount of a catalyst comprising (1) at least one quaternary organic onium iodide compound containing at least 6 carbon atoms and having a melting temperature not exceeding about 225° C. and the formula

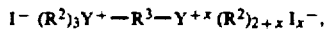

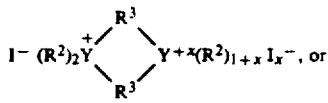

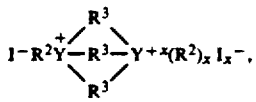

wherein
each $R^2$ is independently selected from hydrogen, alkyl or substituted alkyl moieties having up to about 20 carbon atoms, cycloalkyl or substituted cycloalkyl having about 5 to 20 carbon atoms, aryl or substituted aryl having about 6 to 20 carbon atoms; ferrocenyl; or when Y is P, each $R^2$ also may be selected from alkoxy of up to about 20 carbon atoms, cycloalkoxy of about 5 to 20 carbon atoms, aryloxy of 6 to 10 carbon atoms or halogen; two or three $R^2$ substituents collectively may represent joined hydrocarbylene groups which form a mono- or poly-cyclic ring with the Y atom to which they are bonded;

each $R^3$ is independently selected from hydrocarbylene moieties or substituted hydrocarbylene moieties;

x is 0 or 1, and

Y is N, P or As; (2) at least one organometallic compound having the formula

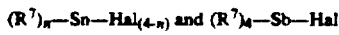$(R^7)_n$—Sn—Hal$_{(4-n)}$ and $(R^7)_4$—Sb—Hal wherein each $R^7$ independently is selected from alkyl or substituted alkyl moieties having up to about 20 carbon atoms, cycloalkyl or substituted cycloalkyl having about 5 to 20 carbon atoms, aryl or substituted aryl having about 6 to 20 carbon atoms;

Hal is bromo or iodo; and n is 1, 2, 3 or 4.

23. Process according to claim 22 wherein the catalyst comprises (1) about 0.5 to 20 weight percent, calculated as weight iodide and based on the total weight of the catalyst of at least one quaternary ammonium or phosphonium iodide, (2) about 0.02 to 20.0 weight percent, based on the total weight of the catalyst, of an organotin (IV) halide containing about 3 to 24 carbon atoms and having the formula

$(R^7)_n$—Sn—I$_{(4-n)}$ wherein each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3; and (3) an essentially non-acidic catalyst support material.

24. Process according to claim 22 wherein the catalyst comprises a melt of (1) at least one quaternary ammonium or phosphonium iodide, (2) at least one organotin (IV) halide containing about 3 to 24 carbon atoms and having the formula

$(R^7)_n$—Sn—I$_{(4-n)}$ wherein each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3; wherein the weight ratio of (1):(2) is about 1:100 to 50:1.

25. Process for the isomerization of 3,4-epoxy-1-butene to 2,5-dihydrofuran which comprises contacting 3,4-epoxy-1-butene in the gas phase at a temperature of about 100° to 200° C. and a pressure of about 1.1 to 20 bar with a catalytic amount of a catalyst comprising (1) one or more quaternary ammonium iodides having the formula

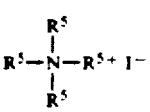

$$R^5\!-\!\overset{\overset{\displaystyle R^5}{|}}{\underset{\underset{\displaystyle R^5}{|}}{N}}\!-\!R^5{}^+\ I^-$$

wherein each $R^5$ substituent is independently selected from alkyl of up to 20 carbon atoms and the quaternary ammonium iodide contains about 16 to 60 carbon atoms; and (2) an organotin (IV) compound containing about 3 to 24 carbon atoms and having the formula $(R^7)_n$—Sn—I$_{(4-n)}$ wherein each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3.

26. Process according to claim 25 for the isomerization of 3,4-epoxy-1-butene to 2,5-dihydrofuran which comprises contacting the 3,4-epoxy-1.butene in the gas phase at a temperature of about 100 to 200° C and a pressure of about 1.1 to 20 bar with a catalytic amount of a catalyst comprising (1) about 0.5 to 20 weight percent, calculated as weight iodide and based on the total weight of the catalyst, of one or more quaternary ammonium iodides having the formula

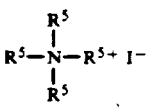

$$R^5\!-\!\overset{\overset{\displaystyle R^5}{|}}{\underset{\underset{\displaystyle R^5}{|}}{N}}\!-\!R^5{}^+\ I^-$$

wherein each $R^5$ substituent is independently selected from alkyl of up to 20 carbon atoms and the quaternary ammonium iodide contains about 16 to 60 carbon atoms, (2) about 0.02 to 20.0 weight percent, based on the total weight of the catalyst, of an organotin (IV) compound containing about 3 to 24 carbon atoms and having the formula $(R^7)_n$—Sn—I$_{(4-n)}$ wherein each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3;

and (3) an essentially non-acidic catalyst support.

27. Process according to claim 25 wherein the catalyst comprises a melt of (1) at least one quaternary ammonium having the formula

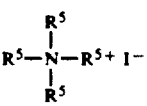

$$R^5\!-\!\overset{\overset{\displaystyle R^5}{|}}{\underset{\underset{\displaystyle R^5}{|}}{N}}\!-\!R^5{}^+\ I^-$$

wherein each $R^5$ substituent is independently selected from alkyl of up to 20 carbon atoms and the quaternary ammonium iodide contains about 16 to 60 carbon atoms and (2) at least one organotin (IV) halide containing about 3 to 24 carbon atoms and having the formula $(R^7)_n$—Sn—I$_{(4-n)}$ wherein each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3;

wherein the weight ratio of (1):(2) is about 1:100 to 50:1.

28. Process for the isomerization of 3,4-epoxy-1-butene to 2,5-dihydrofuran which comprises contacting 3,4-epoxy-1-butene in the gas phase at a temperature of about 100° to 200° C. and a pressure of about 1.1 to 20 bar with a catalytic amount of a catalyst comprising (1) one or more quaternary ammonium iodides having the formula

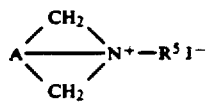

wherein $R^5$ is alkyl of up to about 20 carbon atoms and A is the residue of an azabicycloalkane or diazabicycloalkane having 6 to 12 ring carbon atoms; and (2) an organotin (IV) halide containing about 3 to 24 carbon atoms and having the formula

wherein
each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3.

29. Process according to claim 28 for the isomerization of 3,4-epoxy-1-butene to 2,5-dihydrofuran which comprises contacting 3,4-epoxy-1-butene in the gas phase at a temperature of about 100° to 200° C. and a pressure of about 1.1 to 20 bar with a catalytic amount of a catalyst comprising (1) about 0.5 to 20 weight percent, calculated as weight iodide and based on the total weight of the catalyst, of one or more quaternary ammonium iodides having the formula

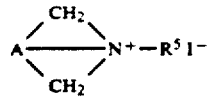

wherein $R^5$ is alkyl of up to about 20 carbon atoms and A is the residue of an azabicycloalkane or diazabicycloalkane having 6 to 12 ring carbon atoms, (2) about 0.02 to 20.0 weight percent, based on the total weight of the catalyst, of an organotin (IV) halide containing about 3 to 24 carbon atoms and having the formula

wherein
each $R^7$ substituent independently is selected from alkyl of up to about 12 carbon atoms, benzyl, phenyl or phenyl substituted with up to 3 substituents selected from lower alkyl, lower alkoxy or halogen ; and n is 2 or 3; and (3) an essentially non-acidic catalyst support.

30. Process according to claim 28 wherein the catalyst comprises a melt of (1) one or more quaternary ammonium iodides having the formula

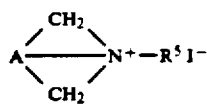

wherein $R^5$ is alkyl of up to about 20 carbon atoms and A is the residue of an azabicycloalkane or diazabicycloalkane having 6 to 12 ring carbon atoms, (2) about 0.02 to 20.0 weight percent, based on the total weight of the catalyst, of an organotin (IV) halide containing about 3 to 24 carbon atoms and having the formula

wherein
each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3;

wherein the weight ratio of (1):(2) is about 1:100 to 50:1.

31. Process for the isomerization of 3,4-epoxy-1-butene to 2,5-dihydrofuran which comprises contacting 3,4-epoxy-1-butene in the gas phase at a temperature of about 100° to 200° C. and a pressure of about 1.1 to 20 bar with a catalytic amount of a catalyst comprising (1) one or more quaternary phosphonium iodides having the formula

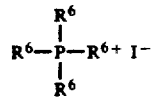

wherein each $R^6$ substituent is independently selected from alkyl of up to 20 carbon atoms, benzyl, phenyl or phenyl substituted with up to 3 substituents selected from lower alkyl, lower alkoxy and halogen and the phosphonium iodide contains about 16 to 60 carbon atoms; and (2) an organo tin (IV) halide containing about 3 to 24 carbon atoms and having the formula

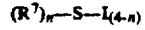

wherein
each $R^7$ substituent independently is selected from alkyl of up to about 12 carbon atoms, benzyl, phenyl or phenyl substituted with up to 3 substituents selected from lower alkyl, lower alkoxy or halogen; and n is 2 or 3.

32. Process according to claim 31 for the isomerization of 3,4-epoxy-1-butene to 2,5-dihydrofuran which comprises contacting 3,4-epoxy-1-butene in the gas phase at a temperature of about 100° to 200° C. and a pressure of about 1.1 to 20 bar with a catalytic amount of a catalyst comprising (1) about 0.5 to 20 weight percent, calculated as weight iodide and based on the total weight of the catalyst, of one or more quaternary phosphonium iodides having the formula

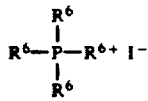

wherein each $R^6$ substituent is independently selected from alkyl of up to 20 carbon atoms, benzyl, phenyl or phenyl substituted with up to 3 substituents selected from lower alkyl, lower alkoxy and halogen and the phosphonium iodide contains about 16 to 60 carbon atoms; (2) about 0.02 to 20.0 weight percent, based on the total weight of the catalyst, of an organotin (IV) halide containing about 3 to 24 carbon atoms and having the formula

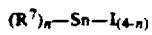

wherein
 each $R^7$ substituent independently is selected from alkyl of up to about 12 carbon atoms, benzyl, phenyl or phenyl substituted with up to 3 substituents selected from lower alkyl, lower alkoxy or halogen; and
 n is 2 or 3; and
(3) an essentially non-acidic catalyst support.

33. Process according to claim 31 wherein the catalyst comprises a melt of (1) one or more quaternary phosphonium iodides having the formula

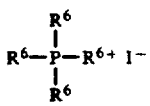

wherein each $R^6$ substituent is independently selected from alkyl of up to 20 carbon atoms, benzyl, phenyl or phenyl substituted with up to 3 substituents selected from lower alkyl, lower alkoxy and halogen and the phosphonium iodide contains about 16 to 60 carbon atoms; (2) an organotin (IV) halide containing about 3 to 24 carbon atoms and having the formula

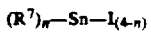

wherein
 each $R^7$ substituent independently is selected from alkyl of up to about 12 carbon atoms, benzyl, phenyl or phenyl substituted with up to 3 substituents selected from lower alkyl, lower alkoxy or halogen; and
 n is 2 or 3;
wherein the weight ratio of (1):(2) is about 1:100 to 50:1.

* * * * *

UNITED STATES PATENT AND TRADEMARK OFFICE
CERTIFICATE OF CORRECTION

PATENT NO. : 5,082,956
DATED : January 21, 1992
INVENTOR(S) : John R. Monnier et al.

It is certified that error appears in the above-identified patent and that said Letters Patent is hereby corrected as shown below:

Column 23, line 55 (Claim 1, line 5), after "onium", ——iodide—— should be inserted.

Column 23, line 60, through column 24, line 6 (Claim 2), the structures should be deleted and the following inserted therefor:

—— 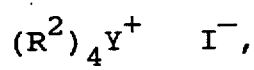

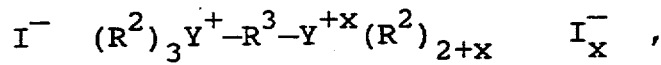

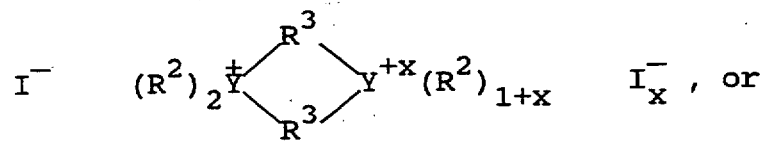

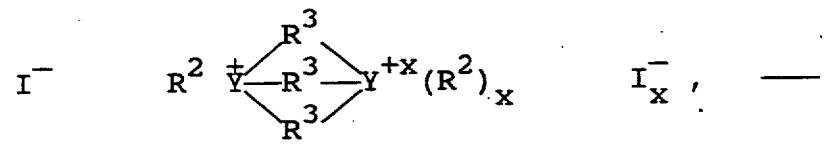

Column 24, line 10 (Claim 2), after "about", ——20—— should be inserted.

UNITED STATES PATENT AND TRADEMARK OFFICE
CERTIFICATE OF CORRECTION

PATENT NO. : 5,082,956
DATED : January 21, 1992
INVENTOR(S) : John R. Monnier et al.

It is certified that error appears in the above-identified patent and that said Letters Patent is hereby corrected as shown below:

Column 24, line 61, through column 25, line 6 (Claim 4), the structures should be deleted and the following inserted therefor:

$$(R^2)_4 Y^+ \quad I^-,$$

$$I^- \quad (R^2)_3 Y^+ - R^3 - Y^{+x}(R^2)_{2+x} \quad I_x^-,$$

$$I^- \quad (R^2)_2 \overset{\pm}{Y} \underset{R^3}{\overset{R^3}{<}} \!\!\! > Y^{+x}(R^2)_{1+x} \quad I_x^-, \text{ or}$$

$$I^- \quad R^2 \overset{\pm}{Y} \!\!\! \underset{R^3}{\overset{R^3}{<}} \!\!\! -R^3 \!\!\! - \!\!\! > Y^{+x}(R^2)_x \quad I_x^-,$$

Column 25, line 11 (Claim 4), after "about", —20— should be inserted.

Column 25, line 16 (Claim 4), after "5 to", —20— should be inserted.

Column 26, lines 1-14 (Claim 6), the structures should be deleted and the following inserted therefor:

UNITED STATES PATENT AND TRADEMARK OFFICE
CERTIFICATE OF CORRECTION

PATENT NO. : 5,082,956
DATED : January 21, 1992
INVENTOR(S) : John R. Monnier et al.

It is certified that error appears in the above-identified patent and that said Letters Patent is hereby corrected as shown below:

— 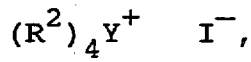

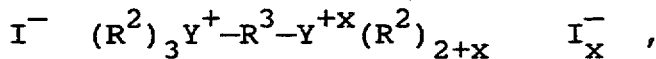

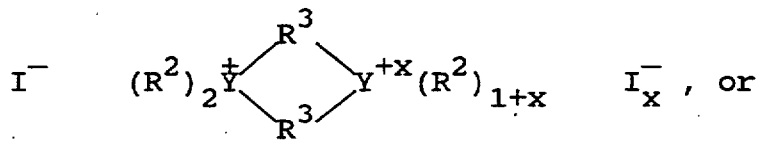

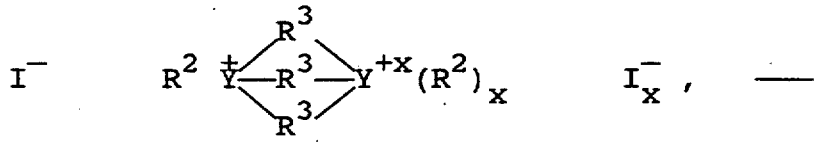

Column 26, line 18 (Claim 6), after "about", ——20—— should be inserted.

Column 26, line 23 (Claim 6), after "5 to", ——20—— should be inserted.

Column 27, lines 13-24 (Claim 8), the structures should be deleted and the following inserted therefor:

— 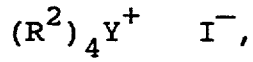

UNITED STATES PATENT AND TRADEMARK OFFICE
CERTIFICATE OF CORRECTION

PATENT NO. : 5,082,956
DATED : January 21, 1992
INVENTOR(S) : John R. Monnier et al.

It is certified that error appears in the above-identified patent and that said Letters Patent is hereby corrected as shown below:

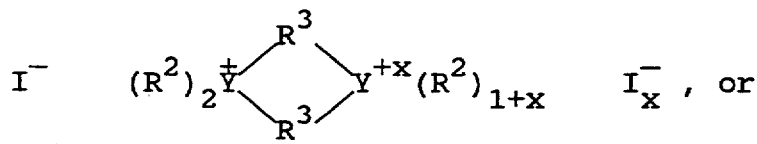

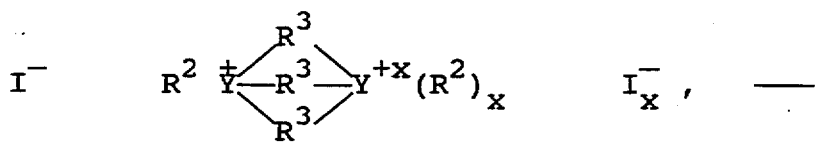

Column 27, lines 55–59 (Claim 9), the structure should be deleted and the following inserted therefor:

— 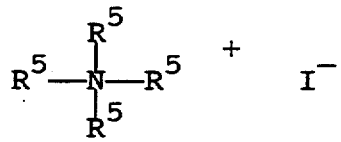 —

Column 28, lines 5–9 (Claim 10), the structure should be deleted and the following inserted therefor:

UNITED STATES PATENT AND TRADEMARK OFFICE
CERTIFICATE OF CORRECTION

PATENT NO. : 5,082,956

DATED : January 21, 1992

INVENTOR(S) : John R. Monnier et al.

It is certified that error appears in the above-identified patent and that said Letters Patent is hereby corrected as shown below:

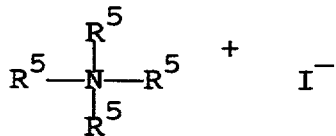

Column 28, lines 23-27 (Claim 12), the structure should be deleted and the following inserted therefor:

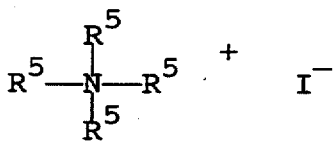

Column 28, lines 40-45 (Claim 13), the structure should be deleted and the following inserted therefor:

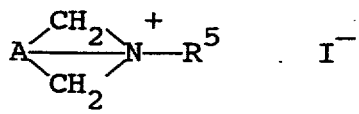

Column 28, lines 55-59 (Claim 14), the structure should be deleted and the following inserted therefor:

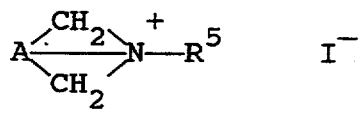

Column 29, lines 4-8 (Claim 16), the structure should be deleted and the following inserted therefor:

UNITED STATES PATENT AND TRADEMARK OFFICE
CERTIFICATE OF CORRECTION

PATENT NO. : 5,082,956

DATED : January 21, 1992

INVENTOR(S) : John R. Monnier et al.

It is certified that error appears in the above-identified patent and that said Letters Patent is hereby corrected as shown below:

— 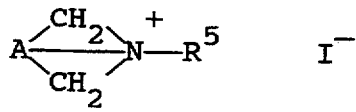 —

Column 29, lines 23-27 (Claim 17), the structure should be deleted and the following inserted therefor:

— 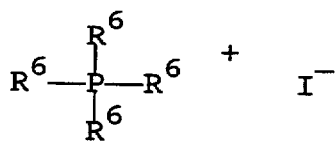 —

Column 29, lines 39-44 (Claim 18), the structure should be deleted and the following inserted therefor:

— 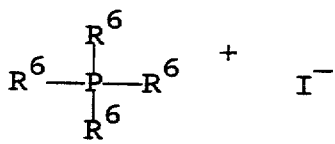 —

Column 29, lines 58-62 (Claim 20), the structure should be deleted and the following inserted therefor:

— 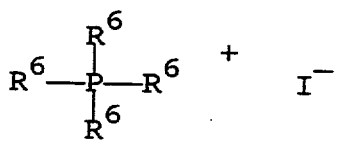 —

UNITED STATES PATENT AND TRADEMARK OFFICE
CERTIFICATE OF CORRECTION

PATENT NO. : 5,082,956

DATED : January 21, 1992

INVENTOR(S) : John R. Monnier et al.

It is certified that error appears in the above-identified patent and that said Letters Patent is hereby corrected as shown below:

Column 30, line 33 (Claim 22), at the end of the line, after "about", ---8--- should be inserted.

Column 30, lines 43-54 (Claim 22), the structures should be deleted and the following inserted therefor:

$$-- \quad (R^2)_4 Y^+ \quad I^-,$$

$$I^- \quad (R^2)_3 Y^+ - R^3 - Y^{+x}(R^2)_{2+x} \quad I_x^-,$$

$$I^- \quad (R^2)_2 Y \underset{R^3}{\overset{R^3}{\diamond}} Y^{+x}(R^2)_{1+x} \quad I_x^-, \text{ or}$$

$$I^- \quad R^2 Y \underset{R^3}{\overset{R^3}{\diamond}} R^3 - Y^{+x}(R^2)_x \quad I_x^-, \quad ---$$

Column 31, lines 61-65 (Claim 25), the structure should be deleted and the following inserted therefor:

UNITED STATES PATENT AND TRADEMARK OFFICE
CERTIFICATE OF CORRECTION

PATENT NO. : 5,082,956
DATED : January 21, 1992
INVENTOR(S) : John R. Monnier et al.

It is certified that error appears in the above-identified patent and that said Letters Patent is hereby corrected as shown below:

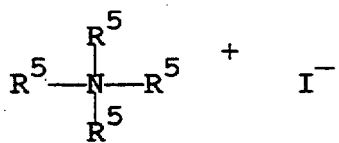

Column 32, lines 25-29 (Claim 26), the structure should be deleted and the following inserted therefor:

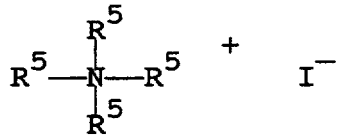

Column 32, lines 52-56 (Claim 27), the structure should be deleted and the following inserted therefor:

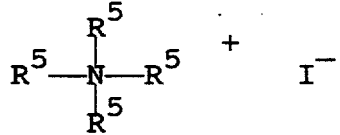

Column 33, lines 14-18 (Claim 28), the structure should be deleted and the following inserted therefor:

UNITED STATES PATENT AND TRADEMARK OFFICE
CERTIFICATE OF CORRECTION

PATENT NO. : 5,082,956

DATED : January 21, 1992

INVENTOR(S) : John R. Monnier et al.

It is certified that error appears in the above-identified patent and that said Letters Patent is hereby corrected as shown below:

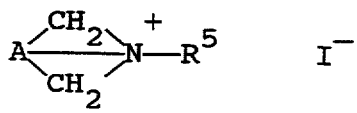

Column 33, lines 46-50 (Claim 29), the structure should be deleted and the following inserted therefor:

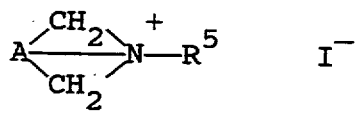

Column 34, lines 5-9 (Claim 30), the structure should be deleted and the following inserted therefor:

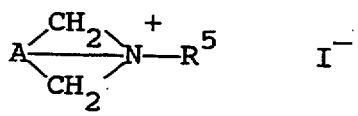

Column 34, lines 36-40 (Claim 31), the structure should be deleted and the following inserted therefor:

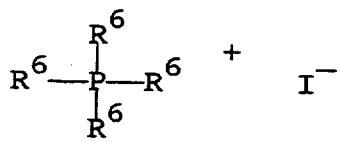

Column 34, line 50 (Claim 31), the structure should be deleted and the following inserted therefor:

UNITED STATES PATENT AND TRADEMARK OFFICE
CERTIFICATE OF CORRECTION

PATENT NO. : 5,082,956
DATED : January 21, 1992
INVENTOR(S) : John R. Monnier et al.

It is certified that error appears in the above-identified patent and that said Letters Patent is hereby corrected as shown below:

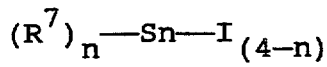

Column 35, lines 1-6 (Claim 32), the structure should be deleted and the following inserted therefor:

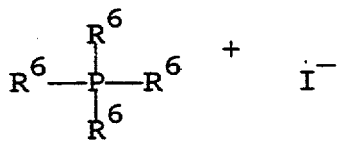

Column 36, lines 5-9 (Claim 33), the structure should be deleted and the following inserted therefor:

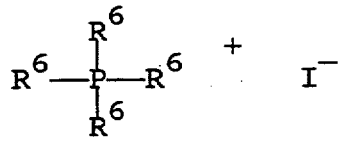

Signed and Sealed this

Fifteenth Day of August, 1995

Attest:

BRUCE LEHMAN

*Attesting Officer*          *Commissioner of Patents and Trademarks*